(12) United States Patent
Reddy et al.

(10) Patent No.: US 9,751,911 B2
(45) Date of Patent: Sep. 5, 2017

(54) SOLOMONAMIDE ANALOGUE COMPOUNDS, PHARMACEUTICALS CONTAINING SOLOMONAMIDE ANALOGUE COMPOUNDS, AND PROCESSES FOR THE PREPARATION THEREOF

(71) Applicant: COUNCIL OF SCIENTIFIC AND INDUSTRIAL RESEARCH, New Delhi (IN)

(72) Inventors: Dumbala Srinivasa Reddy, Maharashtra (IN); Kashinath Komirishetty, Maharashtra (IN); Vasudevan Natarajan, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/442,094

(22) PCT Filed: Nov. 27, 2013

(86) PCT No.: PCT/IN2013/000716
§ 371 (c)(1),
(2) Date: May 11, 2015

(87) PCT Pub. No.: WO2014/083578
PCT Pub. Date: Jun. 5, 2014

(65) Prior Publication Data
US 2015/0291659 A1    Oct. 15, 2015

(30) Foreign Application Priority Data
Nov. 27, 2012   (IN) ............. 2850/DEL/2012

(51) Int. Cl.
| | | |
|---|---|---|
| A61K 38/06 | (2006.01) |
| C07K 5/087 | (2006.01) |
| C07D 245/06 | (2006.01) |
| C07C 231/12 | (2006.01) |
| C07D 339/06 | (2006.01) |
| C07K 1/00 | (2006.01) |
| C07K 5/06 | (2006.01) |
| C07K 5/062 | (2006.01) |
| A61K 38/00 | (2006.01) |

(52) U.S. Cl.
CPC .......... *C07K 5/0812* (2013.01); *C07C 231/12* (2013.01); *C07D 245/06* (2013.01); *C07D 339/06* (2013.01); *C07K 1/00* (2013.01); *C07K 5/06* (2013.01); *C07K 5/06026* (2013.01); *A61K 38/00* (2013.01)

(58) Field of Classification Search
None
See application file for complete search history.

(56) References Cited

FOREIGN PATENT DOCUMENTS

WO    WO 2011/034659 A2    3/2011

OTHER PUBLICATIONS

Festa et al., "Solomonamides A and B, New Anti-inflammatory Peptides from theonella swinhoei", Organic Letters, vol. 13, No. 6, Mar. 18, 2011, pp. 1532-1535.
International Preliminary Report on Patentability for International Application No. PCT/IN2013/000716, dated Sep. 25, 2015.
PCT International Search Report and Written Opinion for PCT/IN2013/000716, mailed Feb. 11, 2014, 16 pgs.
Carmen Festa et al., "Solomonamides A and B, New Ani-inflamatory Peptides from Theonella swinhoei", Organic Letters, 2011, vol. 13, No. 6, pp. 1532-1535.
K. Kashinath et al., "Studies toward the Synthesis of Potent Anti-inflammatory Peptides Solomonamides A and B; Synthesis of a Macrocyclic Skeleton and Key Fragment 4-Amino-6-(2'-amino-4'-hydroxyphenyl)-3-hydroxy-2-methyl-6-oxohexanoic Acid (AHMOA)", Organic Letters, 2012, vol. 14, No. 24, pp. 6222-6225.
Carmen Festa, "Secondary metabolites from natural sources: chemical and Pharmacological characterization", Dottorato Di Ricerca In "Scienza Del Farmaco". XXIII CICLO 2007/2010, pp. 1-243.
C. Li, L. Wang, P. Li, W. Zhou, "Palladium-Catalyzed *ortho*-Acylation of Acetanilides with Aldehydes through Direct-C-H Bond Activation", in Chem. Eur. J. 2011, 17, pp. 10208-10212.

*Primary Examiner* — James H Alstrum Acevedo
*Assistant Examiner* — Sergio Coffa
(74) *Attorney, Agent, or Firm* — Patterson Thuente Pedersen, P.A.

(57) ABSTRACT

Solomanamide analogs of Formula-I having anti-inflammatory activity, and viable synthetic routes for the preparation of such analogs, including the synthesis of macrocyclic core of Salomanamide analogs. The Solomanamide analogs of Formula-I or their pharmaceutical salt may be provided in a pharmaceutical composition and administered in an effective amount for the treatment of inflammation and/or pain.

4 Claims, 3 Drawing Sheets

SOLOMONAMIDE ANALOGUE COMPOUNDS, PHARMACEUTICALS CONTAINING SOLOMONAMIDE ANALOGUE COMPOUNDS, AND PROCESSES FOR THE PREPARATION THEREOF

RELATED APPLICATIONS

The present application is a National Phase entry of PCT Application No. PCT/IN2013/000716, filed Nov. 27, 2013, which claims priority from Indian Application No. 2850/DEL/2012, filed Nov. 27, 2012, said applications being hereby incorporated by reference herein in their entirety.

FIELD OF THE INVENTION

The present invention is generally related to solomonamide analogues, particularly the process for the preparation of solomonamides analogues of Formula I, more particularly the cyclic peptides class of compounds of Formula I. More particularly, the present invention is generally related to novel route for the synthesis of solomonamides analogues thereof as potent anti-inflammatory agents.

BACKGROUND OF THE INVENTION

In early 2011, two cyclic peptides solomonamides A and B with unprecedented chemotype were isolated from the marine sponge *Theonella swinhoei* by Festa, C et al. in an article titled "New Anti-inflammatory Peptides from *Theonella swinhoei*", Org. Lett. 2011, 13, 1532.

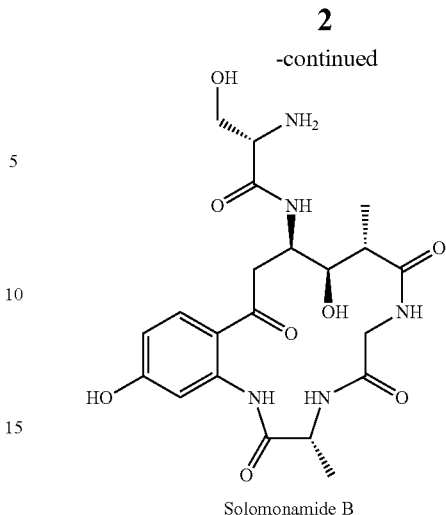

Solomonamide B

According to this Festa et al. article, Solomonamide A significantly reduces (~60%) the inflammation in the carrageenan induced paw edema model. Interestingly, this peptide exhibits its anti-inflammatory property at a very low concentration of 100 µg/kg, in animal-models. Although Solomonamide A displays a dose dependent anti-inflammatory potential under in vivo conditions, the scarcity of the material hampered further development in this direction. Further, Carmen Festa in "*Scienza Del Farmaco*" *XXIII CICLO* 2007/2010 reported a plausible biogenetic origin of ADMOHA [4-amino-3,5-dihydroxy-2-methyl-6-oxa-6-(2'-amino-4'-hydroxy phenyl)]hexanoic acid unit, using 5-hydroxytryptophan (oxitriptan) comprising the reduction of the carboxy group to aldehyde, followed by a Claisen-type condensation with a propionate C3 unit (scheme below) that eventually afford the 4-amino-3,5-dihydroxy-2-methyl-6-oxa-6-(2'-amino-4'-hydroxy phenyl) hexanoic acid (ADMOHA) residue.

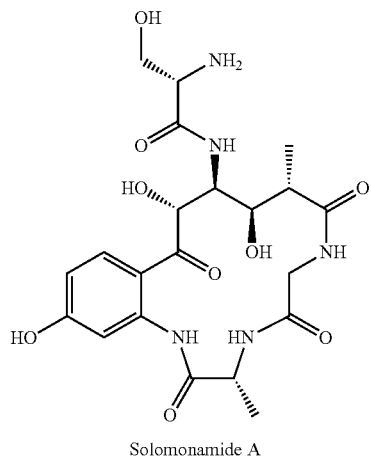

Solomonamide A

Scheme. Plausible biogensis of ADMOHA unit in solomonamide A

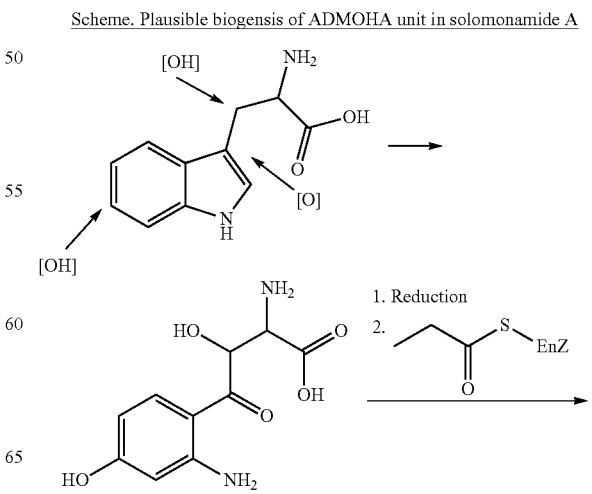

-continued

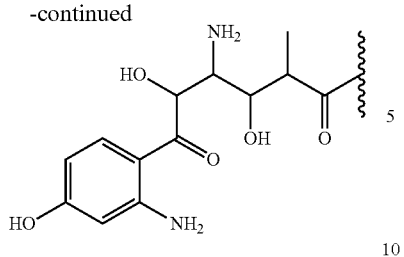

However, the said mechanism is not feasible to achieve absolute stereochemistry of the AHMOA and needs expensive reagents. Accordingly, there is a need for a process for the preparation of solomonamide analogues, solomonamide analogues to meet the growing global demand, and potent and safe solomonamide anaologues that provide desired pharmacological effects, including anti-inflammatory effects.

SUMMARY OF THE INVENTION

According to certain aspects of the present invention, the present invention provides a process for the preparation of solomonamides analogues of Formula-I:

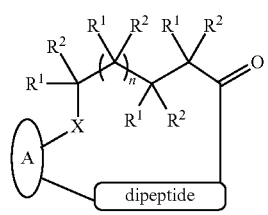

Formula-I

According to certain aspects of the present invention, the present invention is directed to one or more viable synthetic routes for the preparation of solomonamide analogues, and in certain aspects the viable synthetic route has the capability of meeting the growing global demand.

According to certain aspects of the present invention, the present invention provides potent and safe anti-inflammatory analogues of solomonamide chemotype of Formula-I.

According to certain aspects, the present invention provides a process for the synthesis of solomonamide analogue of formula (1a):

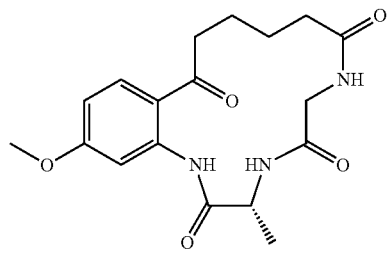

comprising the steps of:
i. acylating 3-methoxy acetanilide and methyl 6-oxo-hexanoate in 1:2 ratio in presence of Pd(TFA)$_2$, TBHP and an organic solvent at a temperature in the range of 90-120° C. to obtain carbonyl-acetanilides compound (4);

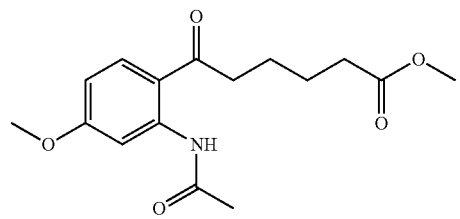

ii. treating compound (4) as obtained in step (i) with 85 to 95% 1,3 propane dithiol and BF$_3$.Et$_2$O in the ratio of 1:1 at temperature in the range of 20 to 35° C. to obtain dithioketal compound (5);

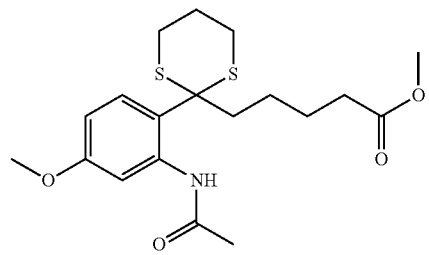

iii. hydrolyzing dithioketal compound (5) as obtained in step (ii) in presence of methanolic HCl to obtain key intermediate (6);
iv. reacting compound (6) with 1 equivalent of Fmoc-D-Alanyl-Chloride (12) to obtain compound (13);
v. hydrolyzing compound (13) in presence of cleavage reagent to give free amine compound (14) followed by treating 1 equivalent of N-Boc glycine to give compound (15);

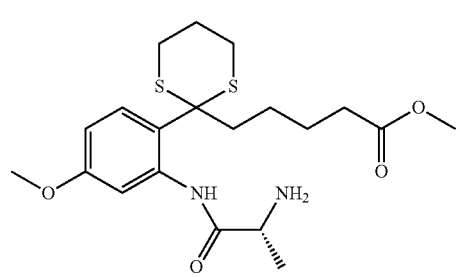

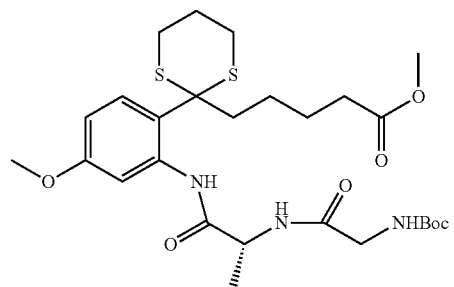

vi. hydrolyzing compound (15) in presence of LiOH to afford acyclic precursor (16);

16

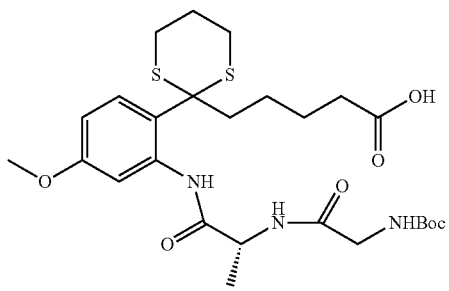

vii. deprotecting the Boc group of compound (16) in the presence of TFA in DCM followed by HATU mediated macrolactamization and subsequently deprotecting in the presence of HgO and BF$_3$.Et$_2$O to furnish solomonamide compound 1a.

In an embodiment of the present invention, dithiol used is selected from the group consisting of (C1-C6)alkane dithiol, aryl dithiol or aralkyl dithiol.

In another embodiment of the present invention, the protection of dithioketal comprises N-acylation in the presence of protected amino acid derivatives including Fmoc, Boc and Cbz protecting groups.

In yet another embodiment of the present invention, the cleavage reagent used is selected from the group consisting of DBU in DMF, piperidine in DMF or THF, piperidine and DBU in DMF, morpholine in DMF, tetra-alkylammonium fluorides in DMF, HOBt, hexamethyleneimine, N-methylpyrrolidine in DMSO or NMP, preferably the cleavage reagent is piperidine in THF.

In yet another embodiment of the present invention, the amino acid used is selected from monopeptide, dipeptide and tripeptide and monopeptide used is selected from the group consisting of glycine, alanine, valine, leucine, isoleucine, norleucine, lysine, serine, threonine, phenylalanine, tyrosine, aspartic acid, cystine, methionine, arginine, tryptophane, histidine, proline, hydroxyproline, iodogorgoic acid; or dipeptide selected from the group consisting of glycyl-glycine, glycyl-alanine, glycyl-valine, glycyl-leucine, glycyl-isoleucine, glycyl-norleucine, glycyl-lysine, glycyl-serine, glycyl-threonine, glycyl-phenylalanine, glycyl-tyrosine, glycyl-aspartic acid, glycyl-cystine, glycyl-methionine, glycyl-arginine, glycyl-tryptophan, glycyl-histidine, glycyl-proline, glycyl-hydroxyproline, glycyl-iodogorgoic acid, alanyl-glycine, alanyl-alanine, alanyl-valine, alanyl-leucine, alanyl-isoleucine, alanyl-norleucine, alanyl-lysine, alanyl-serine, alanyl-threonine, alanyl-phenylalanine, alanyl-tyrosine, alanyl-aspartic acid, alanyl-cystine, alanyl-methionine, alanyl-arginine, alanyl-tryptophanei alanyl-histidine, alanyl-proline, alanyl-hydroxyproline, alanyl-iodogorgoic acid; or tripeptide selected from the group consisting of glycyl-glycyl-glycine, glycyl-glycyl-alanine, glycyl-glycyl-valine, glycyl-glycyl-leucine, glycylglycyl-isoleucine, glycyl-glycyl-norleucine, glyvyl-glycyl-lysine; glycyl-glycyl-serine; glycylglycyl-threonine, glycyl-glycyl-phenylalanine, glycyl-glycyl-tyrosine, glycyl-glycyl-aspartic acid, glycyl-glycyl-cystine, glycyl-glycyl-methionine, glycyl-glycyl-arginine, glycyl-glycyl-tryptophane, glycyl-glycyl-histidine, glycyl-glycylproline, glycyl-glycyl-hydroxyproline, glycyl-glycyl-iodogorgoic acid, glycyl-glycyl-thyroxine, glycyl-glycyl-glycyl-glycine.

In yet another embodiment of the present invention, the hydrolyzing agent is aqueous alkali metal hydroxide selected from the group consisting of NaOH, KOH, LiOH or CsOH.

According to certain aspects, the present invention comprises the solomonamide analogue of formula (1a).

In yet another embodiment, present invention provides a process for the preparation of a compound of Formula II:

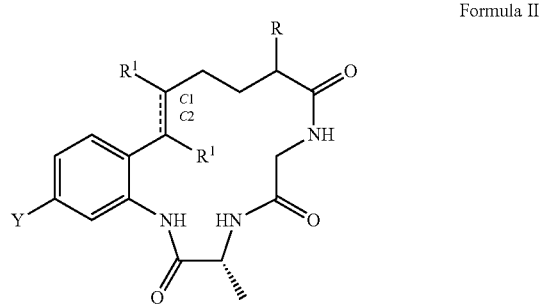

Formula II wherein compounds 1b-1i comprise the following R, Y and R$^1$ substituents:
1b R=H; Y=H; R$^1$=H
1c R=H; Y=H; R$^f$=H
1d R=CH$_3$; Y=H; R$^1$=H
1e R=CH$_3$; Y=H; R$^1$=H
1f R=H; Y=OCH$_3$; R$^1$=H
1g R=H; Y=OCH$_3$; R$^1$=H
1h R=H; Y=H; R$^1$=OH
1i R=H; Y=OCH$_3$; R$^1$=OH wherein the bond between C1 and C2 is a double bond for compounds 1b, 1d and 1f, the bond between C1 and C2 is a single bond for compounds 1c, 1e, 1g, 1h and 1i, and the said process comprising the steps of:

i. coupling of halo-aniline compound (2') with Boc-Gly-D-Ala-OH dipeptide in the presence of a coupling agent and solvent to obtain a halo-dipeptide complex (17'), optionally followed by Stille coupling to obtain vinyl dipeptide intermediate;

ii. refluxing the halo-dipeptide complex compound of step (i) with 2,2,2-trichloroethyl hex-5-enoate (19) in presence of a catalyst to obtain intermediate compound (20');

iii. converting intermediate compound (20') by reacting with 20% TFA in DCM to obtain 1b, 1d and 1f; and iv. reacting compounds 1b, 1d and/or 1f with EtOH, Pd/C for 10 h to obtain compounds 1c, 1e and/or 1g, respectively; or v. reacting compounds 1b, and/or 1f with OsO4 and NMO, t BuOH-water to obtain compounds 1h and/or 1i, respectively.

In yet another embodiment of the present invention, the halo aniline compounds used is selected from the group consisting of o-halo aniline, m-haloanilline, p-halo aniline, halo-o-anisidine, halo-m-anisidine, halo-p-anisidine wherein the halo group is selected from the group consisting of Cl, I, F or Br.

In yet another embodiment of the present invention, the coupling agents used is selected from the group consisting of HATU, HOBt, HOAt TATU, PyBOP in a suitable base selected from the group consisting of disopropyl ethylamine, tertiary butyl amine, methylamine, triethylamine or ammonia.

In yet another embodiment of the present invention, the catalyst is a metal based catalyst, wherein the metal is selected from the group consisting of Ru, Pd, Pt, Rh, Ag, Au, Ni or Cu and the catalyst used is selected from the group consisting of [(1,3-Bis-(2,4,6-trimethylphenyl)-2-imidazolidinylidene)dichloro(o-isopropoxyphenylmethylene)ruthenium] or Palladium (II) acetate.

In yet another embodiment of the present invention, the solvent used is selected from the group consisting of DCM, THF, Ethyl acetate, Acetone, DMF, Acetonitrile, DMSO, isopropanol, n-propanol, ethanol, methanol, n-butanol, tert-butanol or mixtures thereof or aqueous combination thereof, or non polar organic solvent such as chloroform, toluene, diethyl ether, cyclohexane, hexane, 1,4 dioxane or mixtures thereof.

In certain aspects, the present invention is directed at a compound of Formula II chosen from compounds 1b to 1i:

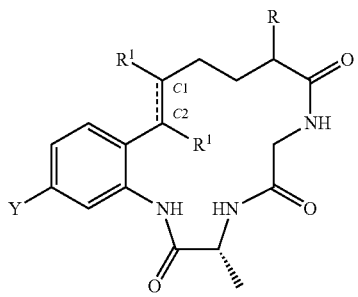

Formula II wherein compounds 1b-1i comprise the following R, Y and $R^1$ substituents:
1b R=H; Y=H; $R^1$=H
1c R=H; Y=H; $R^1$=H
1d R=$CH_3$; Y=H; $R^1$=H
1e R=$CH_3$; Y=H; $R^1$=H
1f R=H; Y=$OCH_3$; $R^1$=H
1g R=H; Y=$OCH_3$; $R^1$=H
1h R=H; Y=H; $R^1$=OH
1i R=H; Y=$OCH_3$; $R^1$=OH and wherein the bond between C1 and C2 is a double bond for compounds 1b, 1d and 1f, and the bond between C1 and C2 is a single bond for compounds 1c, 1e, 1g, 1h and 1i.

In yet another embodiment, present invention provides compounds of Formula-I:

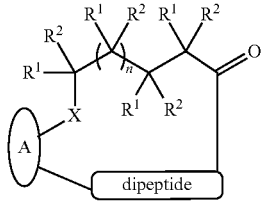

Formula-I wherein the 'Ring A' substituent may be present or absent, and when present the 'Ring A' substituent is selected from the group consisting of a substituted or an unsubstituted aryl, a substituted or an unsubstituted heteroaryl, a substituted or an unsubstituted cycloalkyl, a substituted or an unsubstituted bicyclic, or a substituted or an unsubstituted heterocyclic compound;

wherein the 'dipeptide' substituent is selected from the group consisting of two natural or unnatural amino acids which may include beta amino acids;

wherein the 'X' substituent is selected from the group consisting of O, $NR^a$, S, —S(O), $S(O)_2$, C(O), C(O)O, C(O)$NR^a$, $CR^aR^b$; the bond between the 'X' substituent and an adjacent carbon atom optionally represents double bond; the bond between the 'X;' substituent and an adjacent carbon atom is optionally part of a 3 to 6-membered cycle which may contain 1 or 2 hetero atoms;

wherein the '$R^1$' and '$R^2$' substituents are independently selected from the group consisting of H, OH, OR, $NR^a$, alkyl, aralkyl, substituted or unsubstituted heteroatoms, wherein the '$R^1$' and '$R^2$' substituents are amino acids; wherein the '$R^1$' and '$R^2$' substituents are attached to carbon atom optionally expresses chirality;

wherein n is 0, 1, 2, or 3;

wherein the 'R' substituent is selected from the group consisting of alkyl, aralkyl, C(O)$OR^a$, or C(O)$NR^aR^a$;

'$R^a$' is selected from the group consisting of H, OH, alkyl, aralkyl; and

'$R^b$' is selected from the group consisting of H, OH, alkyl, aralkyl, OR, $NR^aR^a$.

In yet another embodiment of the present invention, representative compounds of Formula II comprise:

(R)-16-methoxy-3-methyl-3,4,6,7,9,10,11,12-octa-hydro-1H-benzo[h][1,4,7]triazacyclo-pentadecine-2,5,8,13-tetraone (1a)

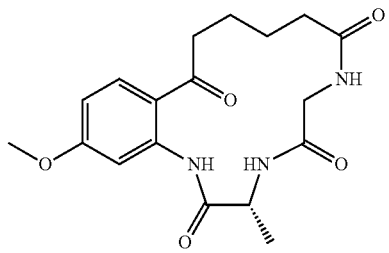 [SMILES: COc1ccc2c(c1)NC(=O)[C@@H](C)NC(=O)CNC(=O)CCCCC2=O]

(R,E)-3-methyl-3,4,6,7,10,11-hexahydro-1H-benzo[h][1,4,7]triazacyclopentadecine-2,5,8(9H)-trione (1b)

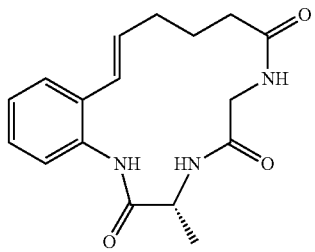 [SMILES: C[C@H]1NC(=O)CNC(=O)CCC/C=C/c2ccccc2NC1=O]

(R)-3-methyl-3,4,6,7,10,11,12,13-octahydro-1H-benzo[h][1,4,7]triazacyclopentadecine-2,5,8(9H)-trione (1c)

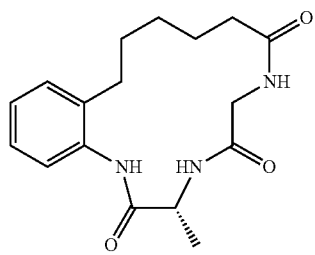 [SMILES: C[C@H]1NC(=O)CNC(=O)CCCCCc2ccccc2NC1=O]

(3R,9S,E)-3,9-dimethyl-3,4,6,7,10,11-hexahydro-1H-benzo[h][1,4,7]triazacyclopentadecine-2,5,8(9H)-trione (1d)

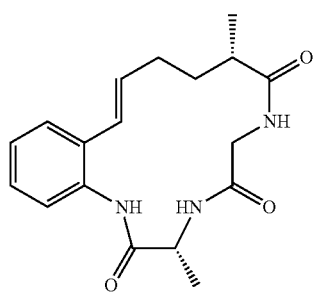 [SMILES: C[C@H]1CC/C=C/c2ccccc2NC(=O)[C@@H](C)NC(=O)CNC1=O]

(3R,9S)-3,9-dimethyl-3,4,6,7,10,11,12,13-octahydro-1H-benzo[h][1,4,7]triazacyclopentadecine-2,5,8(9H)-trione (1e)

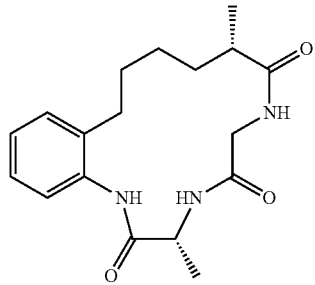 [SMILES: C[C@H]1CCCCc2ccccc2NC(=O)[C@@H](C)NC(=O)CNC1=O]

(R,E)-16-methoxy-3-methyl-3,4,6,7,10,11-hexahydro-1H-benzo[h][1,4,7]triazacyclopentadecine-2,5,8(9H)-trione (1f)

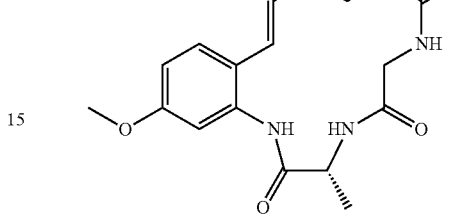

(R)-16-methoxy-3-methyl-3,4,6,7,10,11,12,13-octahydro-1H benzo[h][1,4,7]triazacyclopentadecine-2,5,8(9H)-trione (1g)

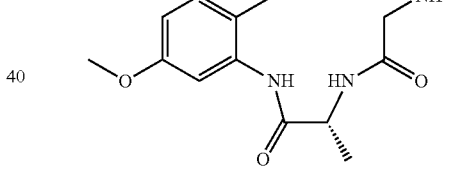

(3R)-12,13-dihydroxy-3-methyl-3,4,6,7,10,11,12,13-octahydro-1H-benzo[h][1,4,7]-triazacyclopentadecine-2,5,8(9H)-trione (1h)

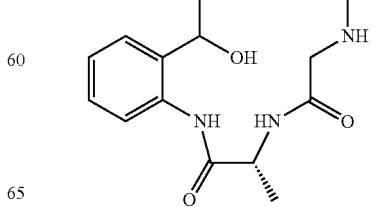

(3R)-12,13-dihydroxy-16-methoxy-3-methyl-3,4,6,7,
10,11,12,13-octahydro-1H-benzo[h][1,4,7]triazacy-
clopentadecine-2,5,8(9H)-trione (1i)

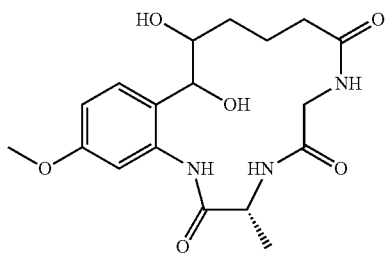 [SMILES: COc1ccc2c(c1)NC(=O)[C@@H](C)NC(=O)CNC(=O)CCCC(O)C2O]

In yet another embodiment, the present invention provides a pharmaceutical composition comprising compound of Formula-I or its pharmaceutically acceptable salts along with pharmaceutically acceptable excipients and/or vehicles, for treatment of inflammation and pain in a mammal caused due to Cox I and Cox II enzymes, wherein the pharmaceutically acceptable salt is selected from the group consisting of hydrochloric acid, hydrobromic acid, nitric acid, sulfuric acid, phosphoric acid, benzenesulfonic acid, methanesulfonic acid, ethanesulfonic acid, toluenesulfonic acid, formamidine sulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid succinic acid, or salts of sodium, potassium, calcium, magnesium and ammonium.

In yet another embodiment, the present invention provides the pharmaceutical compositions containing compounds of Formula-I, which may be administered using any effective amount, any form of pharmaceutical composition and any route of administration effective for the treatment of inflammation and pain. After formulation with an appropriate pharmaceutically acceptable carrier in a desired dosage, as known by those of skill in the art, the pharmaceutical compositions of the present invention can be administered by any means that delivers the active pharmaceutical ingredient(s) to the site of the body whereby it can exert a therapeutic effect on the patient.

In yet another embodiment of the present invention, the excipients or carriers are selected from the group consisting of binders, glidants, fillers, disintegrants, wetting agents and/or lubricants, flavors, colors, preservative, sweeteners, coating agents, etc.

In yet another embodiment of the present invention, the quantity of active compound will range between 0.5% to 90% by weight of the composition.

In yet another embodiment of the present invention, the effective amount of dosage of antibacterial active component will be in the range of about 0.1 to about 100 mg/kg, more preferably about 3.0 mg to about 50 mg/kg of body weight/day.

In yet another embodiment of the present invention, the quantity of the compound of Formula-I used in pharmaceutical compositions of the present invention will vary depending upon the body weight of the patient and the mode of administration and can be of any effective amount to achieve the desired therapeutic effect. The compound of the present invention can also be administered optionally with other anti-inflammatory actives depending on the disease conditions.

In yet another embodiment, the present invention provides use of compounds of Formula-I or its pharmaceutical salts, optionally in association with one or more pharmaceutical carriers for the treatment of inflammation and pain, also useful in treating variety of cancers and metabolic disorders in a subject, wherein the subject as described in the instant invention is a mammal. In certain aspects, the mammal is a human.

In yet another embodiment, the present invention provides feasible strategy and executed key steps toward the total synthesis of highly attractive and potent anti-inflammatory cyclic peptides. Particularly the present invention pertains to a novel route for the synthesis of the macrocyclic core i.e. solomonamide analogues and a key fragment in an orthogonally protected form.

In yet another embodiment, the present invention provides a method of treating or inhibiting or controlling or modulating the activity of Cox I and Cox II enzymes in a subject comprising administering an effective amount of compound of Formula-I or its pharmaceutical salt in association with one or more pharmaceutical carriers.

In yet another embodiment of the present invention, said composition may be formulated into different dosage forms such as tablets, pills, powders, capsules, injections, granules, suspension, syrup, liquid, microemulsion, topical creams, ointments, suppositories, sachets, troches and lozenges.

In yet another embodiment of the present invention, said compound is useful for treatment of inflammation and pain caused due to Cox I and Cox II enzymes.

The above summary of the various representative aspects and embodiments of the present invention is not intended to describe each illustrated aspect or embodiment or every implementation of the present invention. Rather, the aspects and embodiments are chosen and described so that others skilled in the art can appreciate and understand the principles and practices of the present invention. The figures in the detailed description that follow more particularly exemplify these aspects and embodiments.

BRIEF DISCRIPTION OF THE FIGURES

The present invention can be completely understood in consideration of the following detailed description of various aspects and embodiments of the present invention in connection with the accompanying drawings, in which.

ABBREVIATIONS

Figure 1:
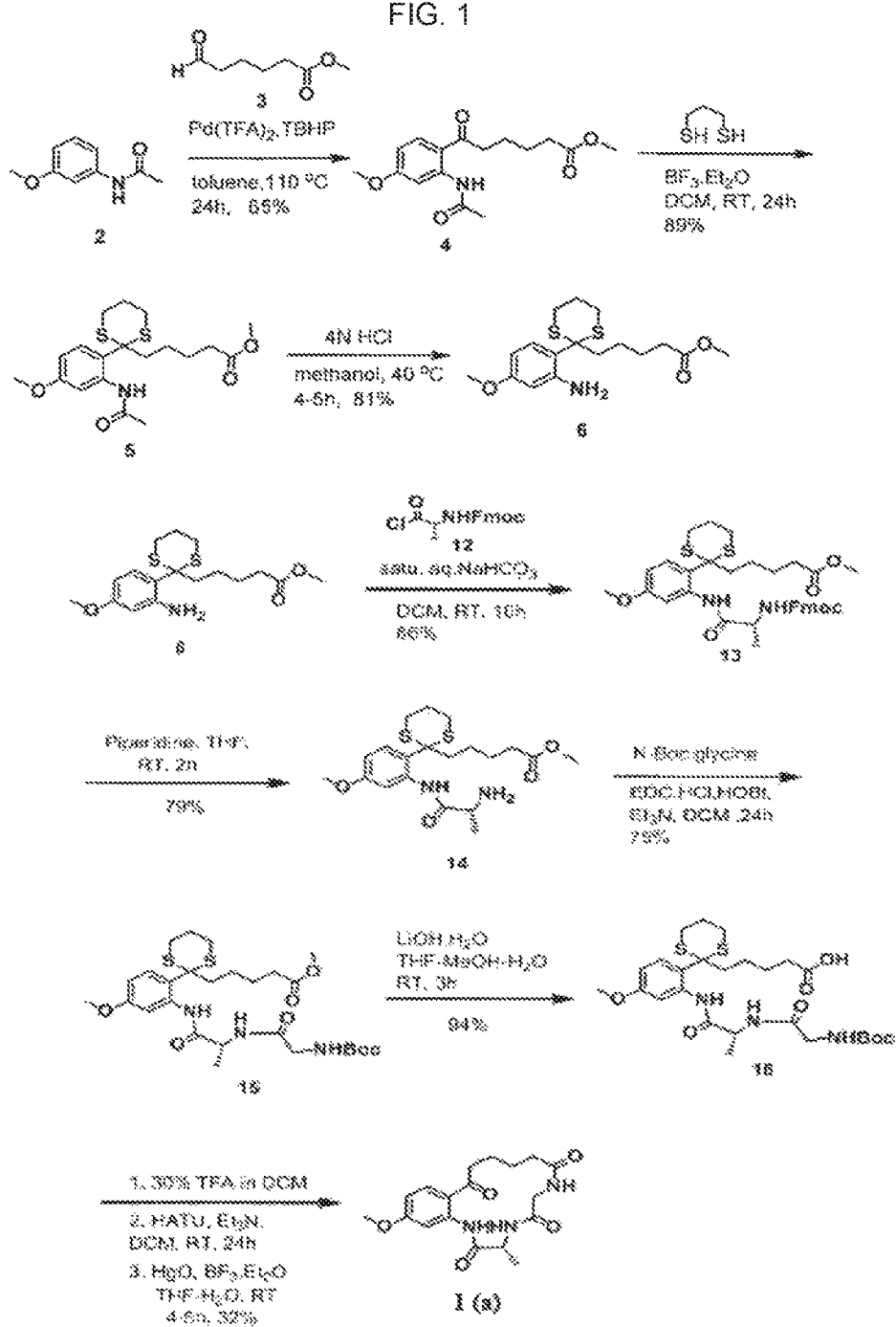
FIG. 1 represents a synthesis pathway of solomonamide analogue of formula Ia, according to certain aspects of the present invention.

As used in the present written description of the present invention, the abbreviations used herein refer to the following:

Fmoc: Fluorenylmethyloxycarbonyl
Boc: tert-Butyloxycarbonyl
Cbz: Carboxybenzyl
TBHP: tert-Butyl hydroperoxide
HATU: (O-(7-azabenzotriazol-1-yl)-N,N,N',N'-tetramethyl-uronium hexafluorophosphate)
DMSO: Dimethyl sulfoxide
DMF: Dimethylformamide
NMP: N-methyl-2-pyrrolidinone
HOBt: N-Hydroxybenzotriazole
DBU: 1,8-Diazabicycloundec-7-ene
TFA: Trifluoroacetic acid
DCC: N,N'-dicyclohexylcarbodiimide
DMAP: Dimethylaminopyridine
THF: Tetrahydrofuran
HOAt: 1-Hydroxy-7-azabenzotriazole
TATU: O-(7-Azabenzotriazol-1-yl)-N,N,N',N'-Tetramethyl-uronium Tetrafluroborate
PyBOP: benzotriazol-1-yl-oxytripyaolidinophosphonium hexafluorophosphate
DCM: Dichloromethane
$BF_3.Et_2O$: boron trifluoride diethyl etherate

DETAILED DESCRIPTION OF THE PRESENT INVENTION

The present invention provides a process for the preparation of solomonamides analogues of Formula-I or their pharmaceutical salt as shown below to assess and identify safe and potential anti-inflammatory agents among the solomonamide chemotype:

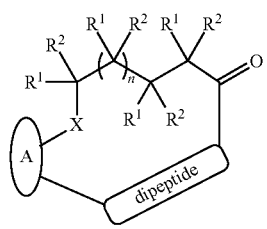

Formula-I wherein the 'Ring A' substituent may be present or absent, and when present the 'Ring A' substituent is selected from the group consisting of a substituted or an unsubstituted aryl, a substituted or an unsubstituted heteroaryl, a substituted or an unsubstituted cycloalkyl, a substituted or an unsubstituted bicyclic, or a substituted or an unsubstituted heterocyclic compound;
wherein the ' dipeptide' substituent is selected from the group consisting of two natural or unnatural amino acids which may include beta amino acids;
wherein the 'X' substituent is selected from the group consisting of O, $NR^a$, S, —S(O), $S(O)_2$, C(O), C(O)O, $C(O)NR^a$, $CR^aR^b$; the bond between the 'X' substituent and an adjacent carbon atom optionally represents double bond; the bond between the 'X; substituent and an adjacent carbon atom is optionally part of a 3 to 6-membered cycle which may contain 1 or 2 hetero atoms;
wherein the '$R^1$' and '$R^2$' substituents are independently selected from the group consisting of H, OH, OR, $NR^a$, alkyl, aralkyl, substituted or unsubstituted heteroatoms, where substituents are amino acids; and/or wherein the '$R^1$' and '$R^2$' substituents are attached to carbon atom optionally expresses chirality;

wherein n is 0, 1, 2, or 3;
wherein the 'R' substituent is selected from the group consisting of alkyl, aralkyl, $C(O)OR^a$, or $C(O)NR^aR^a$;
'$R^a$' is selected from the group consisting of H, OH, alkyl, aralkyl; and
'$R^b$' is selected from the group consisting of H, OH, alkyl, aralkyl, OR, $NR^aR^a$.

Optionally, the dipeptide moiety in compound of Formula-I may be replaced with mono peptide or tripeptide.

The present invention provides novel synthetic route for the preparation of solomonamide analogues to overcome the limitations involved in the availability of the natural cyclic peptide.

The present invention provides one or more processes for synthesis of potent anti-inflammatory cyclic peptides, particularly macrocyclic core of solomonamide analogues of Formula 1a, the process comprising the steps of:
 i. palladium-catalyzed acylation of substituted acetanilides and methyl 6-oxohexanoate in the presence of TBHP and an organic solvent at a suitable temperature, to obtain carbonyl-acetanilides compound;
 ii. protecting carbonyl-acetanilides compound with dithiol in the presence of $BF3.Et_2O$, to yield dithioketal compound;
 iii. protecting of dithioketal compound, followed by deprotecting in the presence of a cleavage reagent to afford a free amine compound;
 iv. coupling of the free amine compound with a protected amino acid/peptide, followed by hydrolyzing to furnish an acyclic precursor;
 v. subjecting the acyclic amino acid to macrolactamization using HATU, followed by deprotection, to obtain a macrocyclic core of solomonamide of formula 1a.

According to the process, Pd catalyzed direct ortho-acylation of substituted acetanilide with methyl-6-oxohexanoate affording the o-acyl acetanilides, wherein $Pd(OCOCF_3)_2$ gave the best result as a Pd catalyst for the coupling reaction in the presence of tert-butyl hydroperoxide (C. Li, L. Wang, P. Li, W. Zhou, in Chem. Eur. J. 2011, 17, 1020). The suitable temperature for acylation is maintained in between 90°-120° C.

The substituents of acetanilides are selected from the group consisting of H, (C1-C6)alkoxy, hydroxyl, preferably acetanilides derivatives are selected from group consisting of 3-methoxy acetanilide, 3-hydroxyl-acetanilide; preferably substituted acetanilides is 3-methoxy acetanilide.

The installation of dithiol is performed in presence of (C1-C6)alkane dithiol, aryl dithiol or aralkyl dithiol at room temperature (20°-35° C.).

The protecting of dithioketal compound is carried out in a two step sequence, firstly deacetylation which is functionalized in presence of alcoholic acid, preferably methanolic HCl at a temperature range of 30°-50° C., followed by N-acylation in the presence of protected amino acid derivatives including Fmoc, Boc and Cbz protecting groups, preferably Fmoc-D-Alanyl-Chloride.

The hydrolysis of the dithioketal compound to obtain the corresponding acid is carried out in the presence of aqueous alkali metal hydroxide such as NaOH, KOH, LiOH, CsOH in a suitable solvent. Further, the HATU mediated macrolactamization is performed in the presence of mixed organic solvent system, such as THF/DMF, $THF/CH_2Cl_2$, and base such as triethylamine, diisopropylethylamine, ammonia and like thereof.

The present invention provides a process for synthesis of a solomonamide analogue of formula Ia, as depicted in FIG. 1. The process comprises preparation of key intermediate 6, which is further converted to desired solomonamide analogue compound 1a. The process for the preparation of key intermediate 6 comprises reacting of compound 2 with compound 3 in the presence of Pd(TFA)$_2$ and TBHP at 110° C. to obtain compound 4, that further treated with 1,3 propane dithiol and BF$_3$.Et$_2$O at room temperature (20°-35° C.) to obtain compound 5, which is subsequently hydrolyzed in the presence of methanolic HCl to obtain key intermediate 6 in high yield. Further compound 6 is treated to yield desired solomonamide compound 1a, which comprises reaction of compound 6 with Fmoc-D-Alanyl-Chloride 12 to obtain compound 13, which is further hydrolyzed in presence of piperdine in THF to give free amine compound 14, followed by treating with N-Boc glycine to give compound 15. The compound 15 is subsequently hydrolyzed in the presence of LiOH to afford compound 16. The deprotection Boc group of compound 16 is carried out in the presence of TFA in DCM followed by HATU mediated macrolactamization to obtain an intermediate, which is subsequently deprotected in the presence of HgO and BF$_3$.Et$_2$O to furnish solomonamide compound 1a.

Figure 2:
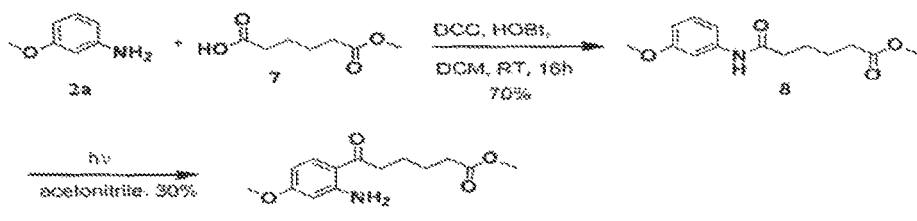
FIG. 2 represents a synthesis pathway of key intermediate 9, according to certain aspects of the present invention.

The present invention provides the preparation of compound 9, a key intermediate useful for the preparation of compound of formula 1a as depicted in FIG. 2. The process comprises, reacting m-Anisidine (2a) with 6-Methoxy-6-oxohexanoic acid (7) in the presence of HOBt in DCC at room temperature (20-35° C.) to obtain compound 8. The compound 8 thus obtained is further converted to desired key intermediate compound 9 by irradiating the same in the presence of acetonitrile or a suitable solvent.

Figure 3:
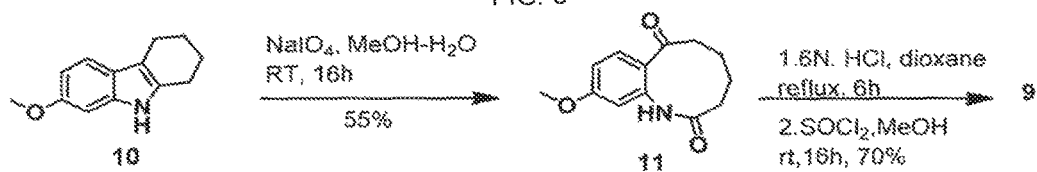
FIG. 3 represents an alternate synthesis pathway of key intermediate 9, according to certain aspects of the present invention.

Alternately, the compound 9 is prepared by oxidative cleavage of compound 10 in methanol in the presence of NaIO$_4$ in water at room temperature (20°-35° C.) to obtain compound 11, further compound 11 in dioxane is hydrolyzed in acidic condition, followed by treatment with SOCl$_2$ in the presence of MeOH at 0° C., and stirred for 16 h at room temperature (20°-35° C.). After completion of starting material, the reaction mass is evaporated to dryness, and neutralized with sat.NaHCO$_3$ sol, followed by extraction and purification to afford compound 9 in high yield (70% or above). The spectral data is found identical with above compound 9 (FIG. 3).

Similarly, compound 9 may be converted to compound of formula 4 by simple acetylation of aniline group and proceed with the subsequent steps as described in FIG. 1, to obtain the macrocyclic core of solomonamide analogue compound 1a.

Figure 4:
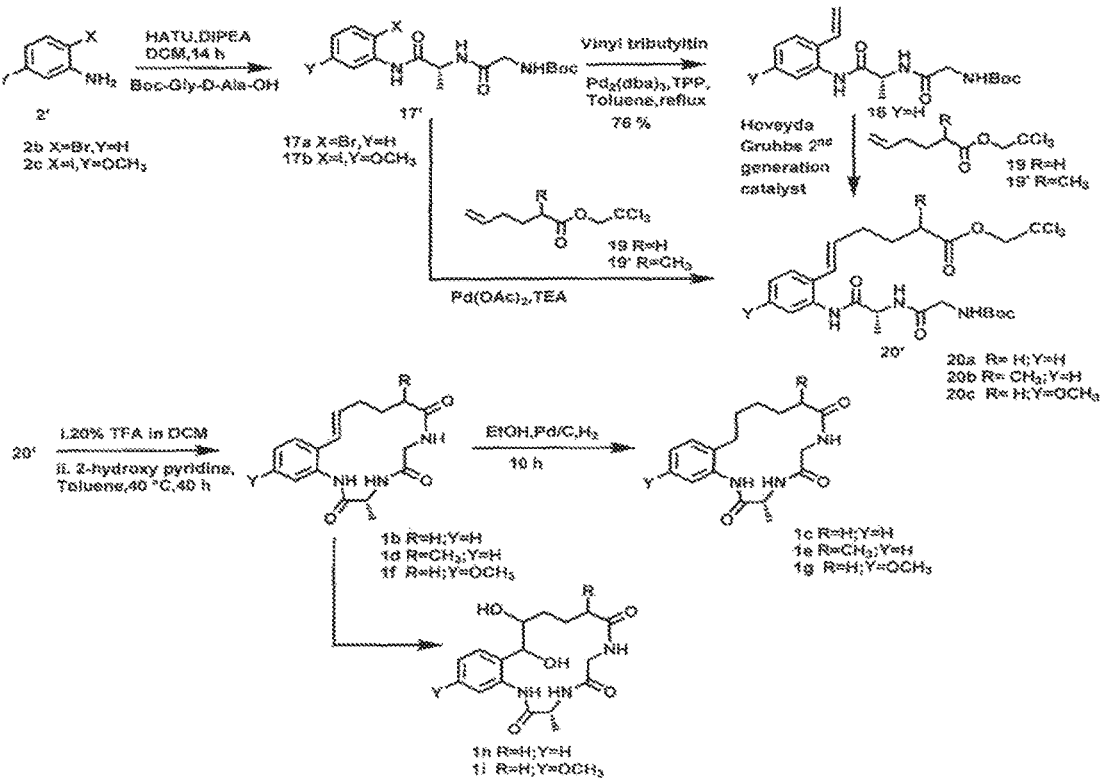
FIG. 4 represents a synthesis pathway of solomonamide analogues of formula I that encompasses the compounds of formula 1b, 1c, 1 d 1e, 1 f, 1g, 1h and 1i, according to certain aspects of the present invention.

The present invention provides a process for the synthesis of solomonamide analogues of Formula-1, encompasses the compounds of formula 1b, 1c, 1d, 1e, 1f, 1g, 1h and 1i respectively, in the presence of 2,2,2-trichloroethyl hex-5-enoate (FIG. 4) comprising the steps of:
  i. coupling of halo-aniline derivatives (2') with dipeptide in presence of coupling agent and organic solvent to obtain halo-dipeptide complex (17'), optionally followed by Stille coupling to obtain vinyl dipeptide intermediate;
  ii. refluxing the dipeptide complex compound of step i) with 2,2,2-trichloroethyl hex-5-enoate (19) in presence of catalyst to obtain intermediate compound (20');
  iii. Further the intermediate compound (20') is converted to solomonamide analogue compounds of formula 1b, 1c, 1d, 1e, 1f, 1g 1h and 1i by employing the known methods.

According to certain aspects of the process of the present invention, the halo aniline derivatives are selected from the group consisting of o-halo aniline, halogen substituted (C1-C6)alkoxy aniline, preferably 2-halo-m-anisidine, or 2-halo m-hydroxy aniline wherein the halo group is selected from the group consisting of Cl, I, F, Br etc.

Dipeptide complex is selected from the group as mentioned herein above, preferably the dipeptide complex is Boc-Gly-D-Ala-OH; where coupling agents are not limited to HATU, HOBt, HOAt TATU, TBTU, PyBOP in base, where suitable base is disopropyl ethylamine, tertiary butyl amine, methylamine, triethylamine, ammonia like thereof.

Further, the addition of 2,2,2-trichloroethyl hex-5-enoate is carried out in the presence of metal based catalyst, wherein the metal is selected from the group consisting of Ru, Pd, Pt, Rh, Ag, Au, Ni, preferably the catalyst is selected from [(1,3-Bis-(2,4,6-trimethylphenyl)-2-imidazolidinylidene)dichloro(o-isopropoxyphenylmethylene)ruthenium] (also referred as Hoveyda Grubbs—2nd generation catalyst) or Pd(II) acetate and TEA. The deprotection of Boc group is carried out in the presence of 10-30% TFA in DCM, followed by cyclization by means of 2-hydroxypyridine in toluene for 35-45 hrs.

It is found that by employing the aniline derivatives as starting material the yield of desired solomonamide analogue is obtained in the range of 33%-95%.

Optionally, the unsaturated solomonamide analogues of formula 1b, 1d and 1f are hydrogenated to saturated solomonamide analogue in the presence of H$_2$ gas and Pd/C catalyst in suitable solvent to obtain compound of formula 1c, 1e and 1g, respectively. Additionally, the macrocyclic core of solomonamide of formula 1b is further converted to other analogues of formula 1h by dihydroxylation.

Figure 5:
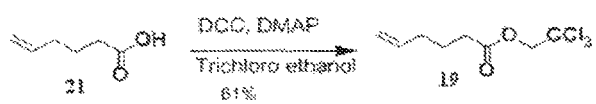
FIG. 5 represents a synthesis pathway of 2,2,2-trichloroethyl hex-5-enoate (19), according to certain aspects of the present invention.

The present invention provides a process for the synthesis of 2,2,2-trichloroethyl hex-5-enoate (19), which comprises reaction of 5-hexenoic acid (21) and trichloro ethanol in CH$_2$Cl$_2$, followed by addition of DCC, DMAP with stirring for 10-12 h at room temperature i.e. 20 to 35° C. The reaction mixture is then filtered and concentrated in vacuo, purification by column chromatography using pet, ether to afford compound 2,2,2-trichloroethyl hex-5-enoate (19) in high yield i.e. more than 60% (FIG. 5).

A process for synthesis of key fragment 31 [4-Amino-6-(20-amino-40-hydroxyphenyl)-3-hydroxy-2-methyl-6-oxo hexanoic acid (AHMOA)], of solomonamide analogue of Formula-I comprising the steps of:
  a) subjecting aldehyde compound 24 to crotylation reaction in the presence of freshly activated CrCl$_2$ to give diastereomers 25a and 25b;
  b) converting 25b to corresponding cyclic carbamates 26b in the presence of NaH at temperature range of 50-70° C. followed by TBS deprotecting and Jones oxidation to afford carboxylic acid 27;
  c) coupling TIPS protected m-amino-phenol 28 with compound 27 in the presence of DCC, HOBt to provide amide compound 29;
  d) photolysing of amide 29 using Hg lamp (254 nm) under dilute conditions in acetonitrile to furnish the photo-Fries rearranged product 30;
  e) oxidative cleavage of olefin in 30 followed by further oxidation furnished carboxylic acid i.e. key fragment 31 in good yield.

Figure 6:
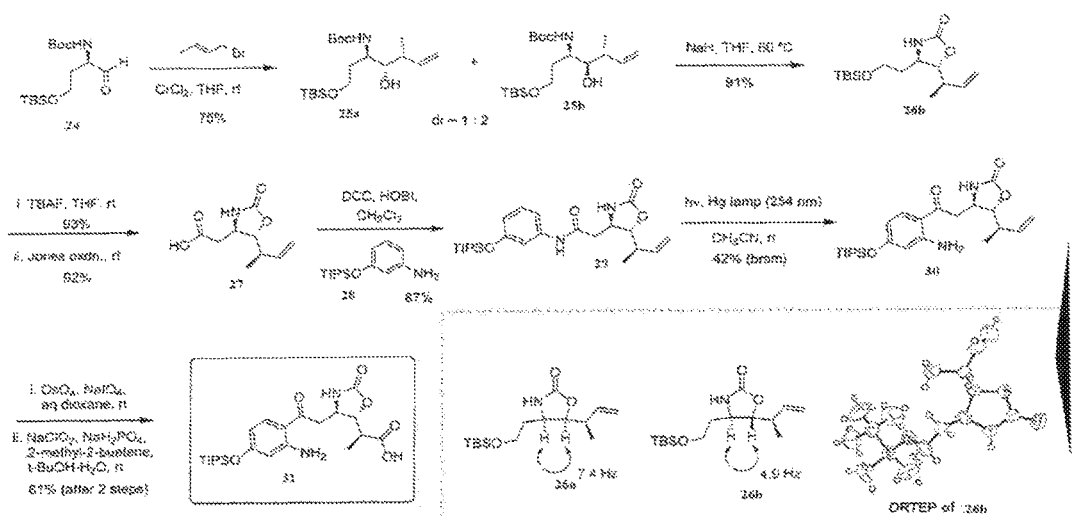
FIG. 6 represents a synthesis pathway of key intermediate 31, according to certain aspects of the present invention.

According to the process, the aldehyde (24) is subjected to a key crotylation reaction to introduce the new chiral centers present in the target molecule. Freshly activated CrCl$_2$ gives a 1:2 ratio of diastereomers (25a) and (25b) in which the desired (25b) is the major compound. The stereochemistry of more deshielded chiral protons is established by comparing their proton coupling constants in the corresponding cyclic carbamates (26a) and (26b), as depicted in FIG. 6.

Further, the undesired isomer 25a can be converted to 25b via an inversion reaction that makes the process cost effective. The complete stereostructure of 26b as drawn is further confirmed by the single X-ray crystal structure. The carboxylic acid 27 prepared from cyclic carbamate 26b (TBS deprotection followed by Jones oxidation) is coupled with TIPS protected m-amino-phenol 28 to provide compound 29. Attempts to form $sp^2$-$sp^2$-C—C bond formation through C—H activation in a similar way to that of the model substrate resulted in very poor yields of the desired product. Therefore, the photolysis of the amide 29 using Hg lamp (254 nm) under dilute conditions in acetonitrile furnished the photo-Fries rearranged product 30 in a highly regioselective manner. Further, oxidative cleavage of olefin in 30 followed by further oxidation furnished carboxylic acid i.e. key fragment 31 in good yield. Thus, the key fragment AHMOA is prepared in a protected form, which will be carried forward to the total synthesis of natural solomonamides.

The organic solvent used in the instant process is not limited to polar solvents such as, DCM, THF, Ethyl acetate, Acetone, DMF, Acetonitrile, DMSO, isopropanol, n-propanol, ethanol, methanol, n-butanol, tert-butanol or mixtures thereof or aqueous combination thereof, and non polar organic solvent such as chloroform, toluene, diethyl ether, cyclohexane, hexane, 1,4 dioxane or mixtures thereof.

It will also be appreciated that, when two or more asymmetric centers are present in the compounds of the present invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the present invention. The present invention encompasses all stereoisomers and enantiomers of compounds of formula I. The present invention further encompasses pharmaceutical salts of the compound of formula I, such as acid addition salts of mineral acids, carboxylic acids and sulfonic acids, for example salts of hydrochloric acid, hydrobromic acid, nitric acid, sulfuric acid, phosphoric acid, benzenesulfonic acid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid and succinic acid.

Pharmaceutically acceptable salts further include salts of customary bases, such as for example alkali metal salts (for example sodium and potassium salts), alkaline earth metal salts (for example calcium and magnesium salts), and ammonium salts derived from ammonia or organic amines. All the intermediates and the final solomonamide analogues involved in the above preparation were characterized by NMR and Mass spectrometry.

Although the route of the synthesis for the preparation of solomonamide analogue(s) depicted by the present invention involves multi steps, however, the yields and the purity of each intermediate and the final compound involved in the instant route makes this as feasible choice for preparation of the novel solomonamide analogues.

EXAMPLES

The following examples are given by way of illustration; and therefore, the following examples should not be construed to limit the scope of the present invention.

Example 1

Methyl 6-(2-acetamido-4-methoxyphenyl)-6-oxohexanoate (4)

N-(3-methoxyphenyl)acetamide 2 (1 g, 6 mmol) and Pd(TFA)$_2$ (100 mg, 0.3 mmol) were loaded in sealed tube with a stirbar. Toluene (12 mL) was added into the tube. The mixture was then stirred for about 1-2 min. Methyl 6-oxohexanoate 3 (1.74 g, 12 mmol), TBHP (6 M in decane, 2 mL) were loaded into the tube. The tube was stirred at 90° C. for 24 h. The reaction mixture was concentrated under reduced pressure and purified by column chromatography (silica gel 100-200 mesh, 1:9 Ethyl acetate:Pet ether) to afford 4 (1.1 g, 65%) as a pale yellow solid.
IR $v_{max}$(film): cm$^{-1}$ 3446, 2925, 2853, 1738, 1733, 1698, 1645, 1615, 1581, 1526, 1435, 1367, 1246, 866; $^1$H NMR (200 MHz, CDCl$_3$): δ 12.12 (bs, 1H), 8.42 (d, 1H, J=2.7 Hz), 7.82 (d, 1H, J=9.0 Hz), 7.03 (dd, 1H, J=2.7, 9.0 Hz), 3.87 (s, 3H), 3.67 (s, 3H), 2.97 (m, 2H), 2.38 (m, 2H), 2.23 (s, 3H), 1.73 (m, 4H); $^{13}$C NMR (100 MHz, CDCl$_3$): δ 202.7, 173.8, 169.9, 164.7, 143.9, 132.7, 114.7, 109.6, 104.0, 55.6, 51.6, 39.2, 33.9, 25.7, 24.5, 24.1; MS: 330 (M+Na)$^+$ Example 2

Methyl 5-(2-(2-acetamido-4-methoxyphenyl)-1,3-dithian-2-yl)pentanoate (5)

To a solution of 4 (1 g, 3.4 mmol) in DCM (20 mL) was added 1,3 propane dithiol (0.85 mL, 8.5 mmol) and BF$_3$.Et$_2$O (1 mL, 8.5 mmol) and stirred at 25° C. for 13 h. The reaction mixture was diluted with DCM (40 mL), added sat. NaHCO$_3$ and the organic layer was dried and concentrated under reduced pressure. The crude was subjected to purification by column chromatography (silica gel 100-200, 15:85 Ethyl acetate:Pet ether) to afford 5 (1.2 g, 89%) as a colorless liquid
IR $v_{max}$(film): cm$^{-1}$ 2949, 1736, 1694, 1525, 1464, 1424; $^1$H NMR (400 MHz, CDCl$_3$): δ 9.81 (bs, 1H), 7.80 (d, J=8.9 Hz, 1H), 7.68 (bs, 1H), 6.66 (dd, J=2.7, 8.9 Hz, 1H), 3.79 (s, 3H), 3.60 (s, 3H), 2.83-2.73 (m, 4H), 2.20-2.17 (m, 2H), 2.15 (s, 3H), 2.11-2.07 (m, 2H), 2.00-1.95 (m, 2H); 1.53-1.46 (m, 2H), 1.30-1.17 (m, 2H); $^{13}$C NMR (100 MHz, CDCl$_3$): δ 173.8, 167.8, 159.5, 137.7, 133.2, 119.8, 110.1, 110.0, 57.4, 55.3, 51.5, 40.5, 33.6, 28.1 (2C), 25.1, 24.9, 24.8, 23.7; MS: 420 (M+Na)$^+$;

Example 3

Methyl 5-(2-(2-amino-4-methoxyphenyl)-1,3-dithian-2-yl)pentanoate (6)

To a stirred solution of 5 (200 mg, 0.5 mmol) in Methanol (5 mL) was added 4N HCl (3 mL) and then heated at 40-50° C. for 4 h. Methanol was removed under reduced pressure, the residue was basified with sat. NaHCO$_3$ (pH=10) and extracted with Ethyl acetate (15 mL×2). The combined organics were dried over Na$_2$SO$_4$, concentrated under reduced pressure and purified by column chromatography (silica gel 100-200, 10:90 Ethyl acetate:Pet ether) to afford 6 (145 mg, 81%) as a colorless liquid.

IR $\nu_{max}$(film): cm$^{-1}$ 3424, 3316, 2949, 2836, 1731, 1617, 1571, 1501, 1437, 1211, 910, 732; $^1$H NMR (200 MHz, CDCl$_3$): δ 7.70 (d, 1H, J=8.7 Hz), 6.33 (dd, 1H, J=8.7, 2.6 Hz), 6.18 (d, 1H, J=2.6 Hz), 4.88 (bs, 2H), 3.77 (s, 3H), 3.62 (s, 3H), 2.66-2.87 (m, 4H), 2.18-2.27 (m, 4H), 1.94-2.00 (m, 2H), 1.47-1.62 (m, 2H), 1.18-1.34 (m, 2H): MS 378 (M+Na)$^+$

Example 4

(R)-methyl-5-(2-(2-(2-((((9H-fluoren-9-yl)methoxy) carbonyl)amino)propanamido)-4-Methoxyphenyl)-1, 3-dithian-2-yl)pentanoate (13)

To a solution of 6 (145 mg, 0.4 mmol) and D-Fmoc-Ala-Cl 12 (148 mg, 0.4 mmol) in dry DCM (5 mL), saturated aq. NaHCO$_3$ (2.5 mL) was added and stirred for 6 h at 25° C. The reaction mixture was diluted with DCM (10 mL) and the organic layer was separated, dried over anhydrous Na$_2$SO$_4$. The crude material obtained after removal of solvent was purified by column chromatography (silica gel 100-200, 3:7 ethyl acetate-pet ether) to afford 13 (175 mg, 66%) as a colorless viscous liquid.

$[\alpha]_D^{27}$=−25.0 (c=0.3, CHCl$_3$); IR $\nu_{max}$(film): cm$^{-1}$ 3273, 1732, 1682, 1610, 1575; $^1$H NMR (200 MHz, CD$_3$OD): δ 7.87-7.69 (m, 5H), 7.42-7.29 (m, 5H), 6.75 (dd, J=2.9, 8.9 Hz, 1H), 4.48-4.15 (m, 4H), 3.77 (s, 3H), 3.52 (s, 3H), 2.72-2.54 (m, 4H), 2.21-1.88 (m, 6H), 1.43 (d, J=7.0 Hz, 3H), 1.38-1.28 (m, 4H); $^{13}$C NMR (100 MHz, CDCl$_3$): δ 173.9, 170.2, 159.5, 155.8, 143.8 (2C), 141.3 (2C), 137.1, 133.3, 127.7 (2C), 127.1 (2C), 125.1(2C), 120.5, 120.0 (2C), 110.6, 109.8, 67.1, 57.4, 55.4 (2C), 51.9, 51.5, 47.2, 40.4, 33.6, 28.0, 24.7 (2C), 23.7, 19.0; MS: 671 (M+Na)$^+$;

Example 5

(R)-Methyl-5-(2-(2-(2-aminopropanamido)-4-methoxyphenyl)-1,3-dithian-2-yl)pentanoate (14)

To a solution of 13 (250 mg, 0.4 mmol) in THF (5 mL), piperidine (0.2 mL) was added and stirred at 23° C. e for 2 h. Reaction mixture was diluted with ethyl acetate (10 mL), washed with water (10 mL) and brine (10 mL), dried over anhydrous Na$_2$SO$_4$. The crude material obtained after removal of solvent was purified by column chromatography (silica gel 100-200, 1:24 methanol-DCM) to afford 13 (140 mg, 85%) as a colorless viscous liquid.

$[\alpha]_D^{25}$=−5.8 (c=0.6, CHCl$_3$); IR $\nu_{max}$(film): cm$^{-1}$ 3245, 2950, 1735, 1679, 1608, 1043; $^1$H NMR (400 MHz, CD$_3$OD): δ 7.84 (d, J=9.0 Hz, 1H), 7.43 (d, J=2.7 Hz, 1H), 6.76 (dd, J=2.7 Hz, 9.0 Hz, 1H), 3.81 (s, 3H), 3.59 (s, 3H), 3.58-3.53 (m, 1H), 2.84-2.79 (m, 4H), 2.23-2.17 (m, 4H), 2.02-1.90 (m, 2H), 1.53-1.45 (m, 2H), 1.39 (d, J=7.0 Hz, 3H), 1.27-1.19 (m, 2H). $^{13}$C NMR (100 MHz, CDCl$_3$): δ 176.5, 175.5, 160.7, 137.9, 134.1, 124.2, 113.1, 110.9, 57.3, 55.8, 52.6, 51.9, 40.8, 34.4, 28.9, 25.9, 25.8 (2C), 25.1, 21.3; MS: 449 (M+Na)$^+$.

Example 6

(R)-Methyl-5-(2-(2-(2-(2-((tert-butoxycarbonyl) amino)acetamido)propanamido)-4-methoxy phenyl)-1,3-dithian-2-yl)pentanoate (15)

To a solution of 14 (120 mg, 0.3 mmol) and Boc-Gly-OH (55 mg, 0.3 mmol) in dry DCM (5 mL) EDC.HCl (48 mg, 0.3 mmol), HOBt (42 mg, 0.3 mmol), Et$_3$N (0.1 mL, 0.6 mmol) were added and stirred for 14 h at 23° C. The reaction mixture was diluted with DCM (10 mL), washed with 1N HCl (10 mL), saturated aq. NaHCO$_3$ solution (10 mL) and dried over anhydrous Na$_2$SO$_4$. The crude material obtained after removal of solvent was purified by column chromatography (silica gel 100-200, 1:30 methanol-DCM) to afford 15 (120 mg, 75%) as a colorless viscous liquid.

$[\alpha]_D^{24}$=18.3 (c=1.0, CHCl$_3$); IR $\nu_{max}$(film): cm$^{-1}$ 3294, 2937, 1718, 1676, 1609, 1169, 1045; $^1$H NMR (400 MHz, CD$_3$OD): δ 7.90 (d, J=8.9 Hz, 1H), 7.41 (d, J=2.3 Hz, 1H), 6.80 (dd, J=2.3, 8.8 Hz, 1H), 4.45 (q, J=7.0 Hz, 1H), 3.84 (s, 2H), 3.80 (s, 3H), 3.60 (s, 3H), 2.81-2.73 (m, 4H), 2.23-2.19 (m, 2H), 2.11-1.91 (m, 4H), 1.50-1.45 (m, 14H), 1.21-1.14 (m, 2H); $^{13}$C NMR (100 MHz, CD$_3$OD): δ 175.7, 172.8, 172.6, 160.8, 158.2, 137.6, 134.7, 123.9, 113.1, 111.3, 80.7, 57.9, 55.8, 52.0, 51.7, 44.7, 41.2, 34.3, 29.0 (2C), 28.7 (3C), 26.0, 25.7, 24.8, 17.7; MS: 606 (M+Na)$^+$.

Example 7

(R)-5-(2-(2-(2-(2-((tert-butoxycarbonyl)amino)acetamido)propanamido)-4-methoxy phenyl)-1,3-dithian-2-yl)pentanoic acid (16)

To a solution of 15 (120 mg, 0.2 mmol) in THF:MeOH (3:2, 5 mL), LiOH (26 mg, 0.6 mmol, in 1 mL water) was added and stirred for 3 h at 25° C. Solvent was removed under reduced pressure and the residue was acidified with 1 N HCl (pH~3) and extracted with ethyl acetate (10 mL×2). The combined organics were dried over anhydrous Na$_2$SO$_4$, concentrated under reduced pressure to afford 16 (110 mg, 94%) as colorless liquid.

$[\alpha]_D^{25}$=−5.0 (c=0.5, CHCl$_3$); IR $\nu_{max}$(film): cm$^{-1}$ 3307, 2933, 1714, 1669, 1610, 1245, 1045; $^1$H NMR (400 MHz, CD$_3$OD): δ 7.88 (d, J=8.8 Hz, 1H), 7.40 (bs, 1H), 6.77 (dd, J=2.5, 8.8 Hz, 1H), 4.46 (q, J=7.3 Hz, 1H), 3.83 (s, 2H), 3.79 (s, 3H), 2.87-2.72 (m, 4H), 2.19-2.07 (m, 4H), 2.09-1.93 (m, 2H), 1.48-1.43 (m, 14H), 1.22-1.20 (m, 2H); $^{13}$C NMR (100 MHz, CD$_3$OD): δ 177.7, 175.6, 173.2, 173.0, 161.1, 138.0, 135.1, 124.3, 113.5, 111.7, 81.0, 58.3, 56.2, 52.1, 45.1, 41.7, 35.0, 31.2, 29.4 (3C), 26.4, 26.3, 25.3, 21.2, 18.2; MS: 592 (M+Na)$^+$.

Example 8

(R)-16-Methoxy-3-methyl-3,4,6,7,9,10,11,12-octahydro-1H-benzo[h][1,4,7]triazacyclopentadecine-2, 5,8,13-tetraone (1a)

To a solution of 16 (40 mg, 0.07 mmol) in DCM (3 mL), TFA (0.9 mL) was added and stirred at 23° C. for 3 h. After completion of the reaction (monitored by TLC), the reaction mixture was concentrated under reduced pressure and the residue was taken up in dry DCM (14 mL), HATU (80 mg, 0.21 mmol) and Et$_3$N (0.05 mL, 0.35 mmol) were added and the resulting reaction solution was stirred at room temperature for 16 h. Reaction mixture was diluted with DCM (10 mL) and washed with 1N HCl (5 mL) and saturated aq. NaHCO$_3$ solution (5 mL). The organic layer was dried over anhydrous Na$_2$SO$_4$, concentrated under reduced pressure. The residue (20 mg, 0.04 mmol) obtained after the evaporation of the solvent was dissolved in THF-water (85:15, 3 mL), HgO (22 mg, 0.1 mmol) and BF$_3$.Et$_2$O (0.01 mL, 0.1 mmol) were added and stirred at room temperature for 4 h. The reaction mixture was filtered and the filtrate was diluted with ethyl acetate (5 mL), washed with brine (5 mL), dried over anhydrous Na$_2$SO$_4$. The crude material obtained after removal of solvent was purified by column chromatography (silica gel 230-400, 1:19 methanol:DCM) to afford 1a as a white solid (8 mg, 32% over 3 steps).

Mp=158-160° C.; [α]$_D^{24}$=29.0 (c=0.2, CHCl$_3$); IR ν$_{max}$ (film): cm$^{-1}$ 2924, 2854, 1632, 1540, 1040; $^1$H NMR (400 MHz, CD$_3$OD): δ 8.21 (d, J=2.8 Hz, 1H), 7.97 (d, J=9.2 Hz, 1H), 6.71 (dd, J=9.2, 2.8 Hz, 1H), 4.54 (d, J=15.1 Hz, 1H), 4.30 (q, J=7.4 Hz, 1H), 3.85 (s, 3H), 3.68 (d, J=15.1 Hz, 1H), 3.01-2.98 (m, 2H), 2.11-1.96 (m, 2H), 1.79-1.58 (m, 4H), 1.49 (d, J=7.4 Hz, 3H); $^{13}$C NMR (100 MHz, CD$_3$OD): δ 203.3, 175.8, 173.5, 171.3, 165.3, 142.8, 133.6, 117.0, 109.6, 105.4, 55.5, 52.1, 43.4, 38.3, 36.1, 26.9, 21.4, 16.6; MS: 384 (M+Na)$^+$.

Example 9

Methyl 6-((3-methoxyphenyl)amino)-6-oxohexanoate (8)

To a solution of 2a (2 g, 16.26 mmol) and 6-Methoxy-6-oxohexanoic acid 7 (2.8 g, 17.88 mmol) in DCM (30 ml) HOBt (2.4 g, 17.88 mmol) was added at 0° C. followed by DCC (3.6 g, 17.88 mmol). This reaction mass was stirred at 22° C. for 16 h. Reaction mass was filtered through celite, filtrate was evaporate to dryness, purified by column chromatography (silica gel 230-400, 4:96 Methanol:DCM) to afford 8 as white Solid (3 g, 70%).

$^1$H NMR (200 MHz, CDCl$_3$): δ 7.62 (bs, 1H), 7.34 (bs, 1H), 7.27-7.16 (m, 1H), 7.01-6.97 (d, 1H, J=8.08 Hz), 6.68-6.63 (dd, 1H, J=1.79, 8.37 Hz), 3.79 (s, 3H), 3.68 (s, 3H), 2.40-2.34 (m, 4H), 1.83-1.66 (m, 4H); MS: 288 (M+Na)$^+$.

Example 10

Methyl 6-(2-amino-4-methoxyphenyl)-6-oxohexanoate (9)

Compound 8 (100 mg) was dissolved in acetonitrile (35 ml), solution was purged with Argon for 10 min. This solution was irradiated with Hg lamp (200-400 nm) for 10 h. After removal of the solvent under reduced pressure, the residues were purified by column chromatography (silica gel 100-200, 4:96 Ethyl acetate:Pet ether) to afford 9 as yellow semi-solid (30 mg, 30%).

$^1$H NMR (200 MHz, CDCl$_3$): δ 7.68 (d, 1H, J=8.96 Hz), 6.42 (bs, 1H), 6.42-6.6.20 (dd, 1H, J=2.39 Hz, 9.06 Hz), 6.07-6.06 (d, 1H, J=2.39 Hz), 3.80 (s, 3H), 3.67 (s, 3H), 2.92-2.86 (m, 2H), 2.41-2.34 (m, 2H), 1.76-1.69 (m, 4H); MS: 288 (M+Na)$^+$.

Example 11

10-methoxy-3,4,5,6-tetrahydro-1H-benzo[b]azonine-2,7-dione (11)

To a solution of 10 (3 g, 14.92 mmol) in MeOH:H$_2$O (1:1, 40 ml), NaIO$_4$(3.8 g, 17.92 mmol) in H$_2$O (10 ml), was added at 0° C., stirred at 23° C. for 16h. Solid thus formed was filtered, filtrate was evaporated to dryness, dissolved in EtOAc (200 ml), washed with H$_2$O (25 ml), Brine (15 ml), dried over Na$_2$SO$_4$, evaporated to dryness, purified by column chromatography (silica gel 230-400, 5:95 Methanol: DCM) to afford compound 11 as a light brown solid (1.9 g, 55%).

Example 12

Methyl 6-(2-amino-4-methoxyphenyl)-6-oxohexanoate (9)

To a solution of 11 (1.9 g, 8.15 mmol) in dioxane (15 ml), 6N HCl (8 ml) was added, refluxed for 6h. Reaction was monitored by TLC and after completion of Starting material, reaction mass was evaporated to dryness, to give black solid. It was dissolved in MeOH (40 ml) and SOCl$_2$ (0.72 ml, 9.6 mmol) was added drop wise at 0° C., stirred for 16h at RT. After completion of starting material, reaction mass was evaporated to dryness, neutralized with sat.NaHCO3 sol, extracted with EtOAc (3×25 ml), combined organic layer was washed with H$_2$O (15 ml), Brine (10 ml), dried over Na$_2$SO$_4$, evaporated to dryness, purified column chromatography (silica gel 100-200, 5:95 Ethyl acetate:Pet ether) to afford compound 9 as a light yellow semi solid (1.47 g, 70%). Spectral data was compared with above compound 9 and found that they are identical.

Example 13

Synthesis of tert-butyl(R)-(2-((1-((2-bromophenyl) amino)-1-oxopropan-2-yl)amino)-2-oxoethyl) carbamate (17a)

To a mixture of 2-bromoaniline 2b (1.0 g, 5.8 mmol), Boc-Gly-D-Ala-OH (1.4 g, 5.8 mmol) in 20 mL CH$_2$Cl$_2$. HATU (3.3 g, 8.7 mmol), Diisopropyl ethylamine (3.0 mL) were added and stirred at 24° C. for 14 h, the reaction mixture was diluted with CH$_2$Cl$_2$ (30 mL) and washed with 1N HCl (15 mL) and sat. NaHCO$_3$ solution (15 mL) organic layer was separated, dried over Na$_2$SO$_4$, concentrated under reduced pressure. Purification by column chromatography with EtOAc/CH$_2$Cl$_2$ (2:3) yielded compound 17a (1.2 g, 52%) as a pale yellow sticky liquid.

$^1$H NMR (500 MHz, CD$_3$OD): δ 7.71 (d, J=8.0 Hz, 1H), 7.62 (d, J=7.3 Hz, 1H), 7.35 (t, J=7.3 Hz, 1H), 7.35 (t, J=7.3 Hz, 1H), 4.58 (q, J=7.3 Hz, 1H), 3.78 (s, 2H), 1.49 (d, J=7.3 Hz, 3H), 1.43 (s, 9H); $^{13}$C NMR (125 MHz, CD$_3$OD): δ170.6, 169.7, 155.6, 133.9, 130.9, 126.2, 125.5, 124.5, 116.1, 77.9, 52.9, 48.0, 25.7 (3C), 14.9; MS: 422 (M+Na)$^+$.

Example 14

Synthesis of tert-butyl(R)-(2-oxo-2-((1-oxo-1-((2-vinylphenyl)amino)propan-2-yl)amino)ethyl)carbamate (18)

To a solution of compound 17a (0.5 g, 1.2 mmol) in toluene (10 mL) under argon, vinyl tributyl tin (0.4 mL, 1.3 mmol) followed by Pd$_2$(dba)$_3$ (60 mg, 0.06 mmol), triphenyl phosphine (65 mg, 0.25 mmol) were added and refluxed for 10h. Further reaction mixture was concentrated in vacuo. Purification by column chromatography with EtOAc/ CH$_2$Cl$_2$ (1:3) yielded compound 18 (332 mg, 76%) as a pale yellow solid.

$^1$H NMR (400 MHz, CD$_3$OD): δ 7.62-7.59 (m, 1H), 7.32-7.22 (m, 3H), 6.88 (dd, J=17.8, 11.3 Hz, 1H), 5.75 (d, J=17.8 Hz, 1H), 5.31 (d, J=11.3 Hz, 1H), 4.55 (q, J=7.3 Hz, 1H), 3.75 (s, 2H), 1.48 (d, J=7.3 Hz, 3H), 1.41 (s, 9H); $^{13}$C NMR (100 MHz, CD$_3$OD): δ 171.2, 169.6, 155.7, 132.3, 132.0, 130.6, 126.8, 126.3, 125.0, 124.9, 123.9, 113.4, 77.9, 47.8, 41.8, 25.7 (3C), 15.1; MS: 370 (M+Na)$^+$.

Example 15

Synthesis of 2,2,2-trichloroethyl hex-5-enoate (19)

To a stirred solution of 5-hexenoic acid 21 (1.0 g, 8.7 mmol) and trichloro ethanol (0.84 ml, 8.7 mmol) in 20 mL CH$_2$Cl$_2$, DCC (1.8 g, 8.7 mmol), DMAP (1.0 g, 8.7 mmol) were added and stirred for 10 h at 23° C. reaction mixture was filtered and concentrated in vacuo, purification by column chromatography using pet, ether to afford compound 19 (1.4 g, 61%) as a colorless liquid.
$^1$H NMR (400 MHz, CDCl$_3$): δ 5.83-5.73 (m, 1H), 5.07-5.09 (m, 2H), 4.74 (s, 2H), 2.47 (t, J=7.45 Hz, 2H); 2.13 (q, J=6.99 Hz, 2H), 1.80 (quin, J=6.8, 14.7 Hz); $^{13}$C NMR (100 MHz, CDCl$_3$): δ 171.9, 137.3, 115.7, 95.0, 73.8, 33.1, 32.9, 23.8; MS: 267 (M+Na)$^+$;

Example 16

Synthesis of 2,2,2-trichloroethyl(S)-2-methylhex-5-enoate (19')

Synthesized from (S)-2-methylhex-5-enoic acid by following procedure for the synthesis of 19 in 70% yield as colorless liquid
$^1$H NMR (200 MHz, CDCl$_3$): δ 5.87-5.67 (m, 1H), 5.07-4.94 (m, 2H), 4.73 (s, 2H), 2.70-2.52 (m, 1H); 2.16-2.05 (m, 2H), 1.94-1.76 (m, 1H), 1.64-1.46 (m, 1H), 1.22 (d, J=7.0, 3H); $^{13}$C NMR (50 MHz, CDCl$_3$): δ174.8, 137.5, 115.4, 95.1, 73.8, 38.7, 32.5, 31.2, 16.8; MS: 281 (M+Na)$^+$;

Example 17

Synthesis of 2,2,2-trichloroethyl(R,E)-6-(2-(2-(2-((tert-butoxycarbonyl)amino)acetamido)propanamido)phenyl)hex-5-enoate (20a)

To a stirred solution of compound 18 (0.4 g, 1.1 mmol) and compound 19 (365 mg, 1.5 mmol) in CH$_2$Cl$_2$, Hoveyda Grubbs—2$^{nd}$ generation catalyst (36 mg, 5 mol %) was added and refluxed for 18h, then the reaction mixture was cooled to rt concentrated in vacuo. purification by column chromatography with EtOAc/CH$_2$Cl$_2$ (2:3) yielded compound 20a (295 mg, 45%) as colorless liquid.
$^1$H NMR (400 MHz, CDCl$_3$): δ 8.24 (bs, 1H), 7.73 (d, J=7.2 Hz, 1H), 7.37 (d, J=7.3 Hz, 1H), 7.21 (t, J=7.5 Hz, 1H), 7.11 (t, J=7.5 Hz, 1H), 6.9 (bs, 1H), 6.49 (d, J=15.4 Hz, 1H), 6.11-6.03 (m, 1H), 5.30 (bs, 1H), 4.73 (s, 2H), 4.70-4.66 (m, 1H), 3.85-3.82 (m, 2H), 2.55 (t, J=7.3 Hz, 2H), 2.34 (q, J=6.6 Hz, 1H), 1.91 (quin, J=7.3, 14.5 Hz), 1.48 (d, J=7.3 Hz, 3H), 1.42 (s, 9H); $^{13}$C NMR (100 MHz, CDCl$_3$): δ172.3, 170.3, 169.9, 156.1, 133.8, 133.1, 130.6, 127.8, 126.8, 126.2, 125.5, 123.7, 94.9, 80.6, 73.9, 49.4, 44.5, 33.3, 32.5, 28.3 (3C), 24.0, 17.6; MS: 586 (M+Na)$^+$.

Example 18

Synthesis of 2,2,2-trichloroethyl(S,E)-6-(2-((R)-2-(2-((tert-butoxycarbonyl)amino)acetamido)propanamido)phenyl)-2-methylhex-5-enoate (20b)

Synthesized from 19' and 18 by following procedure for the synthesis of 20a in 35% yield as colorless liquid.
$^1$H NMR (200 MHz, CDCl$_3$): δ 8.22 (bs, 1H), 7.74 (d, J=7.5 Hz, 1H), 7.35 (d, J=7.5 Hz, 1H), 7.20-7.10 (m, 2H), 6.92 (bs, 1H), 6.47 (d, J=15.6 Hz, 1H), 6.12-6.98 (m, 1H), 5.29 (bs, 1H), 4.72 (s, 2H), 4.66-4.62 (m, 1H), 3.83 (bs, 2H), 2.74-2.61 (m, 1H), 2.37-2.24 (m, 1H), 2.02-1.87 (m, 1H), 1.80-1.61 (m, 1H), 1.48 (d, J=6.9 Hz, 3H), 1.42 (s, 9H), 1.28 (d, J=7.0 Hz, 3H); MS: 600 (M+Na)$^+$

Example 19

Synthesis of (R,E)-3-methyl-3,4,6,7,10,11-hexahydro-1H-benzo[h][1,4,7]triazacyclopentadecine-2,5,8(9H)-trione (1b)

To a solution of compound 20a (200 mg, 0.3 mmol) in 10 mL of CH$_2$Cl$_2$ at 0° C. was added 2 ml of trifluroacetic acid. After stirring at 0° C. for 2 h, solvents were evaporated. The residue was dissolved in ethylacetate washed with saturated sodium bicarbonate. The organic layer was concentrated in vacuo and the residue was taken in toluene (50 mL) and 337 mg of 2-hydroxy pyridine was added and stirred at 40° C. for 40 h, concentrated the reaction mixture ethyl acetate 50 mL was added and washed with saturated sodium bicarbonate solution (20 mL), organic phase was concentrated and purified by column chromatography using CH$_2$Cl$_2$/MeOH (19:1) to yield compound 1b (33 mg, 30%) as off white solid.
$^1$H NMR (500 MHz, CD$_3$OD): δ 7.48 (d, J=7.3 Hz, 1H), 7.38 (d, J=7.6 Hz, 1H), 7.23-7.16 (m, 2H), 6.50 (d, J=15.6 Hz, 1H), 6.08-6.02 (m, 1H), 4.40 (q, J=7.3 Hz, 1H), 3.92-3.82 (m, 2H), 2.38-2.35 (m, 2H), 2.31-2.29 (m, 1H), 2.24-2.18 (m, 1H), 1.99-1.95 (m, 1H), 1.78-1.73 (m, 1H), 1.50 (d, J=7.3 Hz, 3H); $^{13}$C NMR (125 MHz, CD$_3$OD): δ176.9, 174.6, 173.4, 135.7, 135.2, 134.0, 129.7, 129.3, 128.6, 128.4, 128.2, 52.7, 45.5, 35.9, 33.1, 24.7, 17.9; MS: 338 (M+Na)$^+$;

Example 20

Synthesis of (3R,9S,E)-3,9-dimethyl-3,4,6,7,10,11-hexahydro-1H-benzo[h][1,4,7]triazacyclopentadecine-2,5,8(9H)-trione (1d)

To a solution of compound 20b (180 mg, 0.3 mmol) in 10 mL of CH$_2$Cl$_2$ at 0° C. was added 2 ml of trifluroacetic acid. After stirring at 0° C. for 2 h, solvents were evaporated. The residue was dissolved in ethylacetate washed with saturated sodium bicarbonate. The organic layer was concentrated in vacuo and the residue was taken in toluene (50 mL) and 296 mg of 2-hydroxy pyridine was added and stirred at 40° C. for 40 h, concentrated the reaction mixture ethyl acetate 50 mL was added and washed with saturated sodium bicarbonate solution (20 mL), organic phase was concentrated and purified by column chromatography using CH$_2$Cl$_2$/MeOH (19:1) to yield compound 1d (25 mg, 25%) as off white solid.
$^1$H NMR (400 MHz, CD$_3$OD): δ 7.45 (t, J=6.7 Hz, 1H), 7.22-7.14 (m, 3H), 6.45 (d, J=15.3 Hz, 1H), 6.11-6.04 (m, 1H), 4.42 (q, J=7.3 Hz, 1H), 4.25 (d, J=14.5 Hz, 1H), 3.51 (d, J=14.5 Hz, 1H), 2.45-2.34 (m, 2H), 2.55-2.18 (m, 1H), 2.24-2.18 (m, 1H), 1.72-1.62 (m, 2H), 1.48 (d, J=7.3 Hz, 3H), 1.08 (d, J=7.0 Hz, 3H); MS: 352 (M+Na)$^+$;

Example 21

Synthesis of (R)-3-methyl-3,4,6,7,10,11,12,13-octahydro-1H-benzo[h][1,4,7]triazacyclopentadecine-2,5,8(9H)-trione (1c)

To a solution of compound 1b (10 mg, 0.03 mmol) in 3 mL ethanol 5 mg of 10% Pd on activated charcoal was added and stirred under hydrogen for 10h, then filtered the reaction mixture and concentrated to yield compound 1c (9 mg, 90%) as off white solid.

¹H NMR (500 MHz, DMSO-d₆): δ 9.06 (bs, 1H), 8.45 (d, J=6.8 Hz, 1H), 8.33-8.31 (m, 1H), 7.56 (d, J=8.3 Hz, 1H), 7.22-7.11 (m, 3H), 4.43-4.40 (m, 1H), 3.82-3.78 (m, 1H), 3.71-3.67 (m, 1H), 2.38-2.32 (m, 2H), 2.13-2.05 (m, 2H), 1.64-1.61 (m, 1H), 1.47-1.35 (m, 5H), 1.32 (d, J=6.6 Hz, 3H); ¹³C NMR (125 MHz, DMSO-d₆): δ173.2, 171.2, 170.7, 136.7, 136.0, 130.2, 126.5, 125.9, 125.2, 49.7, 43.1, 34.8, 31.9, 31.1, 27.8, 24.8, 17.0; MS: 340 (M+Na)⁺;

Example 22

Synthesis of (3R,9S)-3,9-dimethyl-3,4,6,7,10,11,12, 13-octahydro-1H-benzo[h][1,4,7]triazacyclopentadecine-2,5,8(9H)-trione (1e)

To a solution of compound 1d (10 mg, 0.03 mmol) in 3 mL ethanol 5 mg of 10% Pd on activated charcoal was added and stirred under hydrogen for 10h, then filtered the reaction mixture and concentrated to yield compound 1e (8 mg, 80%) as off white solid.

¹H NMR (500 MHz, DMSO-d₆): δ 9.14 (bs, 1H), 8.73 (d, J=7.0 Hz, 1H), 8.49-8.47 (m, 1H), 7.65 (d, J=7.9 Hz, 1H), 7.17-7.12 (m, 2H), 7.08-7.04 (m, 1H), 4.44-4.41 (m, 1H), 4.20-4.16 (m, 1H), 4.06-4.02 (m, 1H), 2.36-2.28 (m, 3H), 1.44-1.33 (m, 3H), 1.30 (d, J=7.0 Hz, 3H), 0.92 (d, J=6.7 Hz, 3H); MS: 354 (M+Na)⁺;

Example 23

Synthesis of (3R)-12,13-dihydroxy-3-methyl-3,4,6, 7,10,11,12,13-octahydro-1H-benzo[h][1,4,7]triazacyclopentadecine-2,5,8(9H)-trione (1h)

To a stirred solution of 1b (25 mg, in tBuOH-water (3 ml, 1:1), NMO (50% aq. Solution) 74 μl and OsO₄ (2.5% in tBuOH) 40 μl were added and stirred for 6h, concentrated the reaction mixture diluted with ethylacetate, washed with saturated sodium thio sulfate and brine, organic layer was concentrated and purified by column chromatography CH₂Cl₂/MeOH (9:1) afforded compound 1h as diastereomeric mixture in quantitative yield.

¹H NMR (500 MHz, CD₃OD) (mixture of diastereomers) δ 7.60-7.56 (m, 2H), 7.37 (bs, 1H), 7.30-7.28 (m, 2H), 6.63 (bs, 1H), 5.39-5.35 (m, 1H), 4.66-4.63 (m, 1H), 4.46-4.42 (m, 1H), 4.00 (d, J=14.6 Hz, 1H), 3.71 (d, J=14.6 Hz, 1H), 3.61-3.58 (m, 2H), 2.36-2.32 (m, 4H), 2.10-2.06 (m, 2H), 1.70-1.62 (m, 6H), 1.53-1.50 (m, 6H); MS: 372 (M+Na)⁺.

Example 24

(R)-tert-butyl(2-((1-((2-iodo-5-methoxyphenyl) amino)-1-oxopropan-2-yl)amino)-2-oxoethyl)carbamate (17b)

To a mixture of 2-iodo 4-methoxy aniline 2c (1.0 g, 4.0 mmol), Boc-Gly-D-Ala-OH (987 mg, 4.0 mmol) in 20 mL CH₂Cl₂. HATU (2.3 g, 6.0 mmol), diisopropyl ethylamine (2.0 mL) were added and stirred for 14 h at 25° C., the reaction mixture was diluted with CH₂Cl₂ (30 mL) and washed with 1N HCl (15 mL) and sat. NaHCO₃ solution (15 mL) organic layer was separated, dried over Na₂SO₄, concentrated under reduced pressure. Purification by column chromatography with EtOAc/CH₂Cl₂ (2:3) yielded compound 17b (1.2 g, 63%) as a yellow color sticky liquid.

¹H NMR (200 MHz, CDCl₃): δ 8.07 (bs, 1H), 7.87 (d, J=2.8 Hz, 1H), 7.60 (d, J=8.8 Hz, 1H), 6.82-6.78 (m, 1H), 6.50 (dd, J=8.8, 2.8 Hz, 1H), 5.16 (bs, 1H), 4.75-4.62 (m, 1H), 3.88 (d, J=6.0 Hz, 2H), 3.79 (s, 3H), 1.49 (d, J=7.3 Hz, 3H), 1.45 (s, 9H); MS: 500 (M+Na)⁺.

Example 25

Synthesis of (R,E)-2,2,2-trichloroethyl 6-(2-(2-(2-((tert-butoxycarbonyl)amino) acetamido) propanamido)-4-methoxyphenyl)hex-5-enoate (20c)

To a solution of compound 19 (500 mg, 2 mmol) and compound 17b (1.0 g, 2.1 mmol) in anhydrous acetonitrile, Pd(OAc)₂ (7 mg, 1.6 mol %) and triethylamine (2.8 mL) were added and heated at 85° C. for 12h, then the reaction mixture was concentrated in vacuo. Purification by column chromatography with EtOAc/CH₂Cl₂ (2:3) yielded compound 20c (800 mg, 66%) as colorless liquid.

¹H NMR (400 MHz, CDCl₃): δ 8.24 (bs, 1H), 7.58-7.54 (m, 1H), 7.12-7.07 (m, 1H), 6.70-6.67 (m, 1H), 6.43 (d, J=16.1 Hz, 1H), 6.00-5.93 (m, 1H), 5.44 (bs, 1H), 4.75 (s, 2H), 4.73-4.69 (m, 1H), 3.91-3.80 (m, 2H), 3.78 (s, 3H), 2.55 (t, J=7.3 Hz, 2H), 2.32 (q, J=7.3 Hz, 1H), 1.91 (quin, J=6.5, 14.7 Hz), 1.48 (d, J=7.3 Hz, 3H), 1.43 (s, 9H); MS: 616 (M+Na)⁺;

Example 26

Synthesis of (R,E)-16-methoxy-3-methyl-3,4,6,7,10, 11-hexahydro-1H-benzo[h][1,4,7]triazacyclopentadecine-2,5,8(9H)-trione (1f)

To a solution of compound 20c (200 mg, 0.3 mmol) in 10 mL of CH₂Cl₂ at 0° C. was added 2 ml of trifluroaceticacid. After stirring at 0° C. for 2 h, solvents were evaporated; the residue was dissolved in ethylacetate washed with saturated sodium bicarbonate. The organic layer was concentrated in vacuo. The residue was taken in toluene (50 mL) and 320 mg of 2-hydroxy pyridine was added and stirred at 40° C. for 40 h, concentrated the reaction mixture in vacuo ethyl acetate 50 ml was added and washed with saturated sodium bicarbonate solution (20 mL), organic phase was concentrated under reduced pressure and purified by column chromatography using CH₂Cl₂/MeOH (19:1) to yield compound 1f (38 mg, 33%) as white solid.

¹H NMR (500 MHz, CD₃OD): δ 7.42 (d, J=9.3 Hz, 1H), 7.10 (d, J=2.3 Hz, 1H), 6.80-6.78 (m, 1H), 6.45 (d, J=15.0 Hz, 1H), 5.99-5.93 (m, 1H), 4.47 (q, J=7.5 Hz, 1H), 3.95-3.85 (m, 2H), 3.80 (s, 3H), 2.38-2.35 (m, 2H), 2.28-2.25 (m, 1H), 2.02-1.96 (m, 1H), 1.82-1.73 (m, 2H), 1.51 (d, J=7.5 Hz, 3H); MS: 368 (M+Na)⁺.

Example 27

Synthesis of (R)-16-methoxy-3-methyl-3,4,6,7,10, 11,12,13-octahydro-1H-benzo[h][1,4,7]triazacyclopentadecine-2,5,8(9H)-trione (1g)

To a solution of compound 1f (20 mg, 0.03 mmol) in 3 mL ethanol 5 mg of 10% Pd on activated charcoal was added and stirred under hydrogen for 10h, then filtered the reaction mixture and concentrated to yield compound 1g (15 mg, 75%) as off white solid.

¹H NMR (200 MHz, CD₃OD): δ 7.96-7.94 (m, 1H), 7.56-7.44 (m, 1H), 7.17-7.07 (m, 1H), 4.10 (q, J=7.0 Hz,

1H), 3.99-3.89 (m, 1H), 3.75 (s, 3H), 3.65-3.60 (m, 1H), 2.55-2.17 (m, 4H), 1.81-1.42 (m, 9H); MS: 370 (M+Na)$^+$.

Example 28

Synthesis of (3R)-12,13-dihydroxy-16-methoxy-3-methyl-3,4,6,7,10,11,12,13-octahydro-1H-benzo[h][1,4,7]triazacyclopentadecine-2,5,8(9H)-trione (1i)

To a stirred solution of 1f (25 mg, in tBuOH-water (3 ml, 1:1), NMO (50% aq. Solution) 67 µl and OsO$_4$ (2.5% in tBuOH) 38 µl were added and stirred for 6h, concentrated the reaction mixture diluted with ethylacetate, washed with saturated sodium thio sulfate and brine, organic layer was concentrated and purified by column chromatography CH$_2$Cl$_2$/MeOH (9:1) afforded compound 1i as diasteromeric mixture in quantitative yield.

$^1$H NMR (400 MHz, CD$_3$OD) (mixture of diastereomers) δ 7.55 (bs, 1H), 7.19 (d, J=7.0 Hz, 1H), 6.81 (d, J=7.0 Hz, 1H), 6.69 (d, J=8.5 Hz, 1H), 6.60 (bs, 1H), 4.83-4.75 (m, 1H), 4.60-4.42 (m, 3H), 4.10-3.89 (m, 2H), 3.77 (bs, 6H), 3.71-3.63 (m, 4H), 2.41-2.15 (m, 4H), 2.12-2.01 (m, 2H), 1.80-1.54 (m, 6H), 1.47-1.40 (m, 6H); MS: 402 (M+Na)$^+$.

Example 29 tert-Butyl((3R,4S,5R)-1-((tert-butyldimethylsilyl)oxy)-4-hydroxy-5-methylhept-6-en-3-yl)carbamate (25a) and tert-butyl((3R,4R,5R)-1-((tert-butyldimethylsilyl)oxy)-4-hydroxy-5-methylhept-6-en-3-yl)carbamate (25b)

Anhydrous chromium (II) chloride (4.6 g, 37.5 mmol) was transferred into a round bottomed flask under argon atmosphere and heated upto 200° C. for 40 min under high vaccum. (R)-tert-butyl(4-((tert-butyldimethylsilyl)oxy)-1-oxobutan-2-yl)carbamate 24 (4.0 g, 12.6 mmol) in THF (40 mL) was added at 0° C. followed by trans-crotyl bromide (2.6 mL, 25 mmol) and the reaction mixture was stirred at 23° C. for 8 h. Reaction mass was quenched with saturated aq. NH$_4$Cl (20 mL) and extracted with Et$_2$O (4×100 mL). The combined organic layer was dried over anhydrous Na$_2$SO$_4$. The crude material obtained after removal of solvent was purified by column chromatography (silica gel 100-200 mesh, 1:15 to 1:10 ethyl acetate-pet ether) to afford 25b and 25a respectively (~2:1 ratio, 75%).

25a: (1.2 g, 26%) as a colourless oil. [α]$_D^{27}$=5.7 (c=0.9, CHCl$_3$); IR ν$_{max}$(film): cm$^{-1}$ 3441, 2958, 2885, 1701, 1500; $^1$H NMR (400 MHz, CDCl$_3$): δ 5.83 (m, 1H), 5.09-5.05 (m, 3H), 3.85 (bs, 1H), 3.70-3.69 (m, 2H), 3.36 (bs, 1H), 2.86-2.85 (m, 1H), 2.30-2.24 (m, 1H), 1.82-1.66 (m, 2H), 1.41 (s, 9H), 1.01 (d, J=6.4 Hz, 3H), 0.88 (s, 9H), 0.04 (s, 6H); $^{13}$C NMR (100 MHz, CDCl$_3$): δ 155.7, 141.0, 115.8, 79.1, 76.6, 59.8, 50.3, 41.2, 31.1, 28.4 (3C), 25.9 (3C), 18.2, 16.9, -5.5 (2C); MS: 396 (M+Na)$^+$;

25b: (2.3 g, 49%) as a colourless oil. [α]$_D^{27}$=7.6 (c=0.4, CHCl$_3$); IR ν$_{max}$(film): cm$^{-1}$ 3443, 2957, 2859, 1716, 1473; $^1$H NMR (400 MHz, CDCl$_3$): δ 5.83-5.78 (m, 1H), 5.10-5.08 (m, 3H), 3.84-3.83 (m, 1H), 3.70-3.67 (m, 2H), 3.32 (bs, 1H), 3.06 (bs, 1H), 2.24-2.22 (m, 1H), 1.81-1.70 (m, 2H), 1.41 (s, 9H), 1.03 (d, J=7.4 Hz, 3H), 0.88 (s, 9H), 0.04 (d, J=1.6 Hz, 6H); $^{13}$C NMR (100 MHz, CDCl$_3$): δ 156.2, 141.0, 115.7, 79.0, 76.3, 60.0, 49.6, 41.6, 35.8, 28.4 (3C), 25.9 (3C), 18.2, 16.9, -5.5 (2C); MS: 396 (M+Na)$^+$;

Example 30

(4R,5R)-5-((R)-But-3-en-2-yl)-4-(2-((tert-butyldimethylsilyl)oxy)ethyl)oxazolidin-2-one (26 b)

To a stirred solution of 25b (0.3 g, 0.8 mmol) in dry THF (10 mL), NaH (60% in mineral oil, 0.070 g, 1.7 mmol) was added at 0° C. then reaction mass was heated at 60° C. for 2 h. The Reaction mass was cooled to 0° C. and quenched with saturated aq. NH$_4$Cl solution (5 mL), extracted with ethyl acetate (2×20 mL), dried over anhydrous Na$_2$SO$_4$. The crude material obtained after removal of solvent was purified by column chromatography (silica gel 100-200 mesh, 3:7 ethyl acetate-pet ether) to afford 26b as a white crystalline solid (0.22 g, 91%).

Mp=60-61° C.; [ ]$_D^{26}$=43.0 (c=0.5, CHCl$_3$); IR ν$_{max}$ (film): cm$^{-1}$ 3242, 2929, 1756, 1256, 1100; $^1$H NMR (400 MHz, CDCl$_3$): δ 6.25 (bs, 1H), 5.78-5.69 (m, 1H), 5.12 (s, 1H), 5.08 (d, J=5.1 Hz, 1H), 4.15 (t, J=4.9 Hz, 1H), 3.70-3.64 (m, 3H), 2.40-2.45 (m, 1H), 1.73-1.64 (m, 2H), 1.09 (d, J=7.4 Hz, 3H), 0.85 (s, 9H), 0.02 (s, 6H); $^{13}$C NMR (100 MHz, CDCl$_3$): δ 159.1, 137.0, 117.1, 85.0, 60.2, 53.4, 41.3, 38.3, 25.8 (3C), 18.1, 15.2, -5.4 (2C); MS: 322 (M+Na)$^+$;

Example 31

2-((4R,5R)-5-((R)-But-3-en-2-yl)-2-oxooxazolidin-4-yl)acetic acid (27)

To a solution of 26b (1.0 g, 3.3 mmol) in THF (20 mL), TBAF (1M in THF, 5 mmol) was added and stirred for 5 h at 23° C. Reaction mass was quenched with saturated aq. NH$_4$Cl solution (10 mL), extracted with ethyl acetate (2×50 mL). The combined organic layer was washed with water (20 mL), brine (20 mL), dried over anhydrous Na$_2$SO$_4$. The crude material obtained after removal of solvent was purified by column chromatography (silica gel 100-200 mesh, 1:19 MeOH-DCM) to afford (4R,5R)-5-((R)-but-3-en-2-yl)-4-(2-hydroxyethyl)oxazolidin-2-one (0.57 g, 93%) colorless oil.

[ ]$_D^{27}$=37.2 (c=1.3, CHCl$_3$); IR ν$_{max}$ (film): cm$^{-1}$ 3310, 2936, 1735, 1420, 1013; $^1$H NMR (400 MHz, CDCl$_3$): δ 6.93 (s, 1H), 5.75-5.66 (m, 1H), 5.12 (d, J=4.2 Hz, 1H), 5.08 (s, 1H), 4.10 (t, J=5.0 Hz, 1H), 3.72-3.61 (m, 4H), 2.45-2.40 (m, 1H), 1.70 (q, J=6.0 Hz, 2H), 1.06 (d, J=6.7 Hz, 3H); $^{13}$C NMR (100 MHz, CDCl$_3$): δ 159.8, 136.9, 117.2, 85.5, 59.03, 53.3, 41.2, 38.0, 14.9;

To a solution of (4R,5R)-5-((R)-but-3-en-2-yl)-4-(2-hydroxyethyl)oxazolidin-2-one (0.5 g, 2.7 mmol) in acetone (20 mL), Jones reagent (0.7 M solution, 15 mL) was added drop wise at 0° C. and the reaction mixture was stirred for 3.5 h at same temperature. Reaction mass was quenched with isopropanol, the solid thus formed was filtered through a celite bed and the filtrate was evaporated to dryness. The crude material was taken up in ethyl acetate (50 mL), washed with water (10 mL) and brine (15 mL), dried over anhydrous Na$_2$SO$_4$ and concentrated under reduced pressure to afford 27 (0.49 g, 92%) as a white solid.

Mp=98-100° C.; [α]$_D^{25}$=56.0 (c=0.5, CHCl$_3$); IR ν$_{max}$ (film): cm$^{-1}$ 3309, 2974, 1732, 1419, 1240; $^1$H NMR (200 MHz, CDCl$_3$): δ 8.84 (bs, 1H), 7.16 (s, 1H), 5.83-5.66 (m, 1H), 5.22 (s, 1H), 5.15 (d, J=5.5 Hz, 1H), 4.19 (t, J=4.9 Hz, 1H), 3.95 (q, J=6.4 Hz, 1H), 2.63 (d, J=6.8 Hz, 2H), 2.58-2.44 (m, 1H), 1.13 (d, J=6.9 Hz, 3H); $^{13}$C NMR (50

MHz, CDCl$_3$): δ 174.0, 160.3, 136.1, 118.0, 84.5, 51.4, 41.0, 39.9, 14.6; MS: 222 (M+Na)$^+$;

Example 32

2-((4R,5R)-5-((R)-But-3-en-2-yl)-2-oxooxazolidin-4-yl)-N-(3-((triisopropylsilyl)oxy)phenyl)acetamide (29)

To a solution of 27 (0.2 g, 1 mmol) and HOBt (0.16 g, 1.2 mmol) in dry DCM (10 mL), DCC (0.25 g, 1.2 mmol) was added at 0° C., stirred for 10 min. Then 3-((triisopropylsilyl)oxy) aniline 28 (0.26 g, 1 mmol) was introduced and stirring continued for 16 h at room temperature. White solid thus formed was filtered through a celite bed, filtrate was evaporated and purified by column chromatography (silica gel 100-200, 1:19 MeOH-DCM) to afford 29 (0.4 g, 87%) as a white solid.

Mp=110-111° C.; [ ]$_D^{25}$=−5.0 (c=0.5, CHCl$_3$); IR ν$_{max}$ (film): cm$^{-1}$ 2945, 2868, 1748, 1668, 1607; $^1$H NMR (400 MHz, CDCl$_3$): δ 7.96 (m, 1H), 7.23 (s, 1H), 7.14 (t, J=7.9 Hz, 1H), 7.00 (d, J=7.6 Hz, 1H), 6.64 (m, 1H), 5.86 (m, 1H), 5.75 (m, 1H), 5.20-5.16 (m, 2H), 4.28 (m, 1H), 4.05 (m, 1H), 2.67-2.50 (m, 3H), 1.31-1.25 (m, 3H), 1.12 (d, J=7.0 Hz, 3H), 1.10 (d, J=7.6 Hz, 18H); $^{13}$C NMR (100 MHz, CDCl$_3$): δ 167.7, 158.4, 156.6, 138.5, 136.4, 129.6, 117.8, 116.1, 112.3, 111.6, 84.3, 51.6, 42.8, 41.3, 17.9 (3C), 14.8, 12.6 (6C); MS: 469 (M+Na)$^+$;

Example 33

(4R,5R)-4-(2-(2-Amino-4-((triisopropylsilyl)oxy)phenyl)-2-oxoethyl)-5-((R)-but-3-en-2-yl)oxazolidin-2-one (30)

Compound 29 (100 mg, 0.2 mmol) was dissolved in dry acetonitrile (150 mL) and purged with argon for 15 min. This solution was irradiated with low pressure Hg vapour lamp (254 nm, 16 W) for 4.5 h. The residue obtained after the removal of the solvent under reduced pressure was purified by column chromatography (silica gel 230-400, 0.4:99.6 MeOH-DCM) to afford 30 (36 mg, 42% brsm) as a white solid.

Mp=131-132° C.; [ ]$_D^{26}$=33.8 (c=0.2, CHCl$_3$); IR ν$_{max}$ (film): cm$^{-1}$ 3437, 3327, 2945, 2869, 1744, 1636, 1619, 1589; $^1$H NMR (400 MHz, CDCl$_3$): δ 7.49 (d, J=8.8 Hz, 1H), 6.30 (bs, 2H), 6.19 (dd, J=8.8 Hz, 2.1 Hz, 1H), 6.10 (d, J=2.1 Hz, 1H), 5.80 (m, 1H), 5.62 (bs, 1H), 5.20-5.16 (m, 2H), 4.23 (t, J=5.2 Hz, 1H), 4.06 (m, 1H), 3.15 (m, 2H), 2.57 (m, 1H), 1.29-1.23 (m, 3H), 1.16 (d, J=6.7 Hz, 3H), 1.10 (d, J=7.3 Hz, 18H); $^{13}$C NMR (100 MHz, CDCl$_3$): δ 197.2, 162.0, 158.2, 153.0, 136.7, 132.8, 117.6, 112.3, 109.8, 106.3, 84.2, 51.1, 44.6, 41.2, 17.8 (3C), 14.9, 12.7 (6C); MS: 469 (M+Na)$^+$;

Example 34

(S)-2-((4R,5R)-4-(2-(2-Amino-4-((triisopropylsilyl)oxy)phenyl)-2-oxoethyl)-2-oxooxazolidin-5-yl)propanoic acid (31)

To a cooled (0° C.) solution of 30 (50 mg, 0.1 mmol) in dioxane-water (3:1, 4 mL) OsO$_4$ (2.5% in t-BuOH, 0.1 mL, 0.01 mmol), NaIO$_4$(96 mg, 0.4 mmol) and 2,6-lutidine (0.03 mL, 0.2 mmol) were added. The reaction mixture was stirred at room temperature for 3 h, filtered, and concentrated under vacuum. The residue obtained was taken up in ethyl acetate (10 mL), washed with aq.Na$_2$S$_2$O$_3$ (5 mL) followed by brine (5 mL), dried over anhydrous Na$_2$SO$_4$, and concentrated under reduced pressure to afford colorless oil.

To this crude material dissolved in t-BuOH-water (5:1, 3 mL), NaH$_2$PO$_4$ (20 mg, 0.16 mmol), 2-methyl-2-butene (0.03 mL, 0.3 mmol) and NaClO$_2$ (10 mg, 0.1 mmol) were added. After the reaction mixture was stirred at 23° C. for 6 h, the reaction mixture was evaporated to dryness, dissolved in ethyl acetate (10 mL), washed with water (5 mL), and dried over anhydrous Na$_2$SO$_4$. The crude material obtained after removal of solvent was purified by column chromatography (silica gel 100-200 mesh, 1:12, MeOH-DCM) to afford 31 (32 mg, 61%) as an off white solid.

Mp=105-106° C.; [α]$_D^{25}$=−80.5 (c=0.5, CHCl$_3$); IR ν$_{max}$ (film): cm$^{-1}$: 3338, 2925, 2854, 1738, 1614, 1519, 1015; $^1$H NMR (400 MHz, CD$_3$OD): δ 7.63 (d, J=8.8 Hz, 1H), 6.23 (d, J=2.2 Hz, 1H), 6.15 (dd, J=2.2, 8.8 Hz, 1H), 4.64-4.59 (m, 1H), 4.23-4.20 (m, 1H), 3.29-3.25 (m, 2H), 2.89-2.83 (m, 1H), 1.29-1.27 (m, 3H), 1.22 (d, J=7.0 Hz, 3H), 1.15-1.11 (m, 18H); $^{13}$C NMR (100 MHz, CD$_3$OD): δ 198.8, 162.9, 161.2, 134.4, 113.6, 110.0, 107.0, 83.8, 53.0, 46.0, 45.5, 18.4 (6C), 13.9 (3C), 12.4. MS: 487 (M+Na)$^+$;

The present invention provides a novel synthetic route for bulk production of naturally occurring valuable compounds. Further the preparation of the solomonamide class of biologically active molecules by means of novel chemical synthesis provides sufficient yield and purity of the desired compounds that emphasizes the economic significance and technical advancement of the instant invention.

The invention claimed is:
1. A compound comprising:
a solomonamide analogue of Formula I

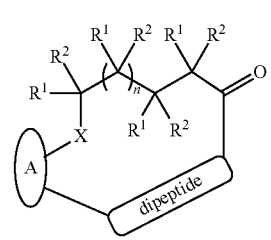

Formula-I wherein the Ring A is selected from the group consisting of a substituted or an unsubstituted aryl, a substituted or an unsubstituted heteroaryl, a substituted or an unsubstituted cycloalkyl, a substituted or an unsubstituted bicyclic compound, or a substituted or an unsubstituted heterocyclic compound;

wherein the dipeptide is selected from the group consisting of two natural amino acids or two unnatural amino acids;

wherein X is selected from the group consisting of O, NR$^a$, S, —S(O), S(O)$_2$, C(O), C(O)O, C(O)NR$^a$, CR$^a$R$^b$;

wherein the bond between X and an adjacent carbon atom is optionally a double bond; and wherein the bond between X and the adjacent carbon atom is optionally part of a 3 to 6-membered cycle having 1 or 2 hetero atoms;

wherein R$^1$ and R$^2$ is independently selected from the group consisting of H, OH, OR, NR$^a$, alkyl, aralkyl, substituted heteroatoms, unsubstituted heteroatoms, and amino acids; and wherein $R^1$ and $R^2$ substituents are attached to carbon atom optionally expresses chirality;

wherein n is 0, 1, 2, or 3;

wherein the 'R' substituent is selected from the group consisting of alkyl, aralkyl, $C(O)OR^a$, or $C(O)NR^aR^a$;

'$R^a$' is selected from the group consisting of H, OH, alkyl, and aralkyl; and

'$R^b$' is selected from the group consisting of H, OH, alkyl, aralkyl, OR, and $NR^aR^a$ with a proviso that when the dipeptide is Gly-D-Ala, Ring A is the substituted aryl, X is C(O) and n is 1, then the solomonamide analogues chosen from

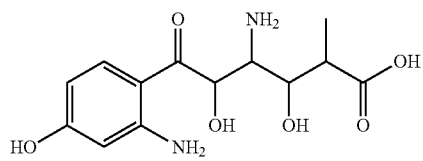

and

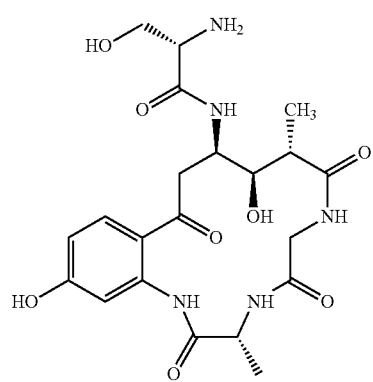

are excluded.

2. The compound of claim 1, wherein said compound is selected from the group consisting of (R)-16-methoxy-3-methyl-3,4,6,7,9,10,11,12-octahydro-1H-benzo[h][1,4,7]triazacyclo-pentadecine-2,5,8,13-tetraone (1a);

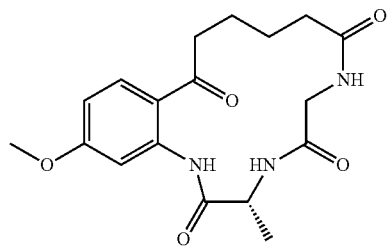 [SMILES: COc1ccc2c(c1)NC(=O)[C@@H](C)NC(=O)CNC(=O)CCCCC2=O]

(R,E)-3-methyl-3,4,6,7,10,11-hexahydro-1H-benzo[h][1,4,7]triazacyclopentadecine-2,5,8(9H)-trione (1b);

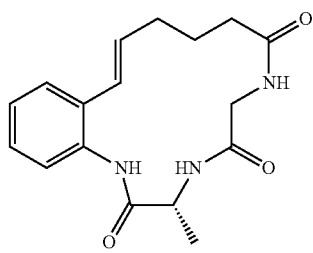 [SMILES: C[C@H]1NC(=O)CNC(=O)CCC/C=C/c2ccccc2NC1=O]

(R)-3-methyl-3,4,6,7,10,11,12,13-octahydro-1H-benzo[h][1,4,7]triazacyclopentadecine-2,5,8(9H)-trione (1c);

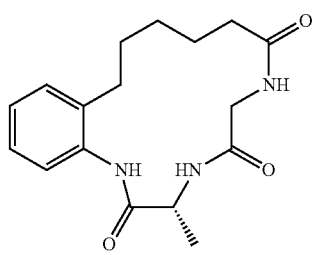 [SMILES: C[C@H]1NC(=O)CNC(=O)CCCCCc2ccccc2NC1=O]

(3R,9S,E)-3,9-dimethyl-3,4,6,7,10,11-hexahydro-1H-benzo[h][1,4,7]triazacyclo-pentadecine-2,5,8(9H)-trione (1d);

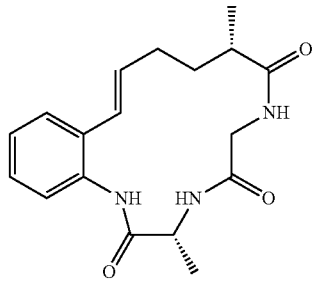 [SMILES: C[C@H]1CC/C=C/c2ccccc2NC(=O)[C@@H](C)NC(=O)CNC1=O]

(3R,9S)-3,9-dimethyl-3,4,6,7,10,11,12,13-octahydro-1H-benzo[h][1,4,7]triazacyclo-pentadecine-2,5,8(9H)-trione (1e);

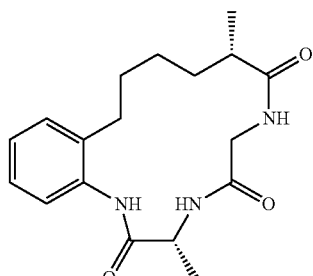

(R,E)-16-methoxy-3-methyl-3,4,6,7,10,11-hexahydro-1H-benzo[h][1,4,7]triazacyclopentadecine-2,5,8(9H)-trione (1 f);

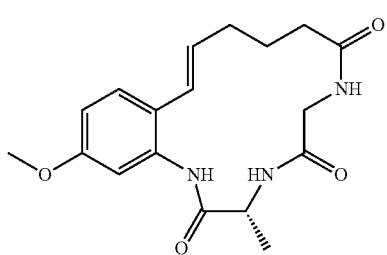 [SMILES: COc1ccc2c(c1)NC(=O)[C@@H](C)NC(=O)CNC(=O)CCC/C=C/2]

(R)-16-methoxy-3-methyl-3,4,6,7,10,11,12,13-octahydro-1H-benzo[h][1,4,7]triazacyclopentadecine-2,5,8(9H)-trione (1g);

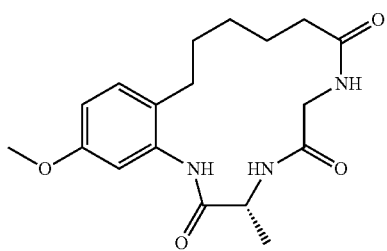 [SMILES: COc1ccc2c(c1)NC(=O)[C@@H](C)NC(=O)CNC(=O)CCCCC2]

(3R)-12,13-dihydroxy-3-methyl-3,4,6,7,10,11,12,13-octahydro-1H-benzo[h][1,4,7]-triazacyclopentadecine-2,5,8(9H)-trione (1h);

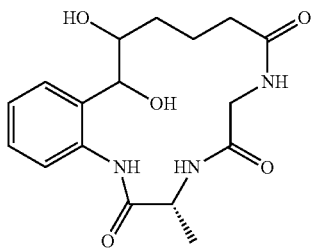 [SMILES: C[C@H]1NC(=O)CNC(=O)CCCC(O)C(O)c2ccccc2NC1=O]

(3R)-12,13-dihydroxy-16-methoxy-3-methyl-3,4,6,7,10,11,12,13-octahydro-1H-benzo[h][1,4,7]triazacyclopentadecine-2,5,8(9H)-trione (1i).

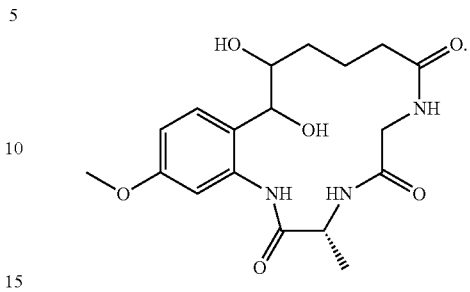

3. A pharmaceutical composition comprising the compound of claim 2 or a pharmaceutically acceptable salt of the compound along with pharmaceutically acceptable excipients and/or vehicles, for treatment of inflammation and pain caused due to Cox I and Cox II enzymes, wherein the pharmaceutically acceptable salt is selected from the group consisting of hydrochloric acid, hydrobromic acid, nitric acid, sulfuric acid, phosphoric acid, benzenesulfonic acid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid, succinic acid, a salt of sodium, a salt of potassium, a salt of calcium, a salt of magnesium and a salt of ammonium.

4. The pharmaceutical composition of claim 3, wherein said composition may be formulated into a dosage form chosen from tablets, pills, powders, capsules, injections, granules, suspension, syrup, liquid, microemulsion, topical creams, ointments, suppositories, sachets, troches and lozenges.

* * * * *

UNITED STATES PATENT AND TRADEMARK OFFICE
CERTIFICATE OF CORRECTION

PATENT NO. : 9,751,911 B2  Page 1 of 1
APPLICATION NO. : 14/442094
DATED : September 5, 2017
INVENTOR(S) : Dumabala Srinivasa Reddy et al.

It is certified that error appears in the above-identified patent and that said Letters Patent is hereby corrected as shown below:

In the Claims

Column 31, Lines 20-45, please delete the existing two elements and insert the following two elements:

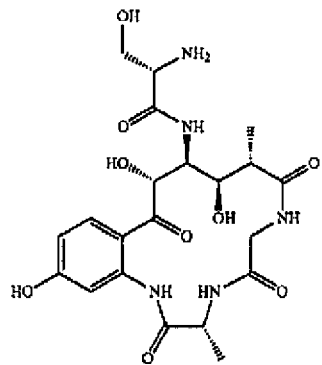

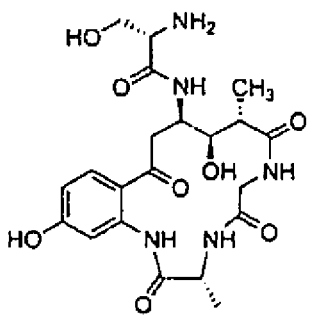

-- --

Signed and Sealed this
Seventeenth Day of October, 2017

Joseph Matal
*Performing the Functions and Duties of the
Under Secretary of Commerce for Intellectual Property and
Director of the United States Patent and Trademark Office*